United States Patent
George et al.

(10) Patent No.: US 7,814,912 B2
(45) Date of Patent: Oct. 19, 2010

(54) DELIVERY METHODS AND DEVICES FOR IMPLANTABLE BRONCHIAL ISOLATION DEVICES

(75) Inventors: Robert M. George, San Jose, CA (US); Ronald R. Hundertmark, San Mateo, CA (US); Michael Hendricksen, Redwood City, CA (US)

(73) Assignee: Pulmonx Corporation, Redwood City, CA (US)

( * ) Notice: Subject to any disclaimer, the term of this patent is extended or adjusted under 35 U.S.C. 154(b) by 1401 days.

(21) Appl. No.: 11/174,040

(22) Filed: Jun. 29, 2005

(65) Prior Publication Data

US 2006/0004305 A1     Jan. 5, 2006

Related U.S. Application Data

(63) Continuation-in-part of application No. 10/723,273, filed on Nov. 25, 2003.

(60) Provisional application No. 60/429,902, filed on Nov. 27, 2002.

(51) Int. Cl.
*A61B 5/08* (2006.01)

(52) U.S. Cl. ............... 128/207.14; 128/200.26; 128/200.24; 600/101; 600/104; 600/127; 600/129; 600/587; 604/19

(58) Field of Classification Search ............ 128/200.24, 128/200.26, 205.23; 600/529, 538, 533, 600/587, 591, 593
See application file for complete search history.

(56) References Cited

U.S. PATENT DOCUMENTS

| | | | |
|---|---|---|---|
| 2,981,254 A | 4/1961 | Vanderbilt | |
| 3,657,744 A | 4/1972 | Ersek | |
| 3,788,327 A | 1/1974 | Donowitz et al. | |
| 3,874,388 A | 4/1975 | King et al. | |
| 4,014,318 A | 3/1977 | Dockum et al. | |

(Continued)

FOREIGN PATENT DOCUMENTS

DE     9205797.7     6/1992

(Continued)

OTHER PUBLICATIONS

Ogoshi Y, Pipe diameter measuring device e.g. for industrial field has expansion member which expands in radial direction to predetermined size corresponding to diameter of expansion operating unit; Oct. 20, 2000; Derwent Acc-No. 2001-019895; abstract.*

(Continued)

*Primary Examiner*—Justine R Yu
*Assistant Examiner*—Clinton Ostrup
(74) *Attorney, Agent, or Firm*—Townsend and Townsend and Crew LLP

(57) ABSTRACT

Disclosed is a sizing device for sizing an inside diameter of a lung passageway. The device includes an elongate shaft configured for positioning in the lung passageway and a sizing element at the distal end of the shaft. The sizing element defines a range of transverse dimensions that correspond to a range of transverse dimensions suitable for use with a predetermined set of bronchial isolation devices. The device is used to determine the suitability of a bronchial isolation device for use in the lung passageway prior to using a separate delivery catheter to deliver the bronchial isolation device into the lung passageway.

15 Claims, 20 Drawing Sheets

U.S. PATENT DOCUMENTS

| | | | |
|---|---|---|---|
| 4,086,665 A | 5/1978 | Poirier | |
| 4,212,463 A | 7/1980 | Repinski et al. | |
| 4,250,873 A | 2/1981 | Bonnet | |
| 4,302,854 A | 12/1981 | Runge | |
| 4,477,930 A | 10/1984 | Totten et al. | |
| 4,483,075 A * | 11/1984 | Kundin | 331/21 |
| 4,566,465 A * | 1/1986 | Arhan et al. | 600/591 |
| 4,586,491 A * | 5/1986 | Carpenter | 600/113 |
| 4,710,192 A | 12/1987 | Liotta et al. | |
| 4,732,152 A | 3/1988 | Wallsten et al. | |
| 4,759,758 A | 7/1988 | Gabbay | |
| 4,795,449 A | 1/1989 | Schneider et al. | |
| 4,808,183 A | 2/1989 | Panje | |
| 4,819,664 A | 4/1989 | Nazari | |
| 4,830,003 A | 5/1989 | Wolff et al. | |
| 4,832,680 A | 5/1989 | Haber et al. | |
| 4,846,836 A | 7/1989 | Reich | |
| 4,850,999 A | 7/1989 | Planck | |
| 4,852,568 A | 8/1989 | Kensey | |
| 4,877,025 A | 10/1989 | Hanson | |
| 4,934,999 A | 6/1990 | Bader | |
| 4,968,294 A | 11/1990 | Salama | |
| 5,010,892 A * | 4/1991 | Colvin et al. | 600/587 |
| 5,061,274 A | 10/1991 | Kensey | |
| 5,116,360 A | 5/1992 | Pinchuk et al. | |
| 5,116,564 A | 5/1992 | Jansen et al. | |
| 5,123,919 A | 6/1992 | Sauter et al. | |
| 5,151,105 A | 9/1992 | Kwan-Gett | |
| 5,161,524 A | 11/1992 | Evans | |
| 5,271,385 A * | 12/1993 | Bailey | 600/214 |
| 5,306,234 A | 4/1994 | Johnson | |
| 5,352,240 A | 10/1994 | Ross | |
| 5,358,518 A | 10/1994 | Camilli | |
| 5,366,478 A | 11/1994 | Brinkerhoff et al. | |
| 5,382,261 A | 1/1995 | Palmaz | |
| 5,392,775 A | 2/1995 | Adkins et al. | |
| 5,409,019 A | 4/1995 | Wilk | |
| 5,411,507 A | 5/1995 | Heckele | |
| 5,411,552 A | 5/1995 | Andersen et al. | |
| 5,413,599 A | 5/1995 | Imachi et al. | |
| 5,417,226 A | 5/1995 | Juma | |
| 5,445,626 A | 8/1995 | Gigante | |
| 5,486,154 A | 1/1996 | Kelleher | |
| 5,499,995 A | 3/1996 | Teirstein | |
| 5,500,014 A | 3/1996 | Quijano et al. | |
| 5,562,608 A | 10/1996 | Sekins et al. | |
| 5,588,424 A | 12/1996 | Insler et al. | |
| 5,645,565 A | 7/1997 | Rudd et al. | |
| 5,660,175 A | 8/1997 | Dayal | |
| 5,662,713 A | 9/1997 | Andersen et al. | |
| 5,683,451 A | 11/1997 | Lenker et al. | |
| 5,697,968 A | 12/1997 | Rogers et al. | |
| 5,755,770 A | 5/1998 | Ravenscroft | |
| 5,800,339 A | 9/1998 | Salama | |
| 5,840,081 A | 11/1998 | Andersen et al. | |
| 5,851,232 A | 12/1998 | Lois | |
| 5,855,587 A | 1/1999 | Hyon et al. | |
| 5,855,597 A | 1/1999 | Jayaraman | |
| 5,855,601 A | 1/1999 | Bessler et al. | |
| 5,944,738 A | 8/1999 | Amplatz et al. | |
| 5,947,997 A | 9/1999 | Pavcnik et al. | |
| 5,954,766 A | 9/1999 | Zadno-Azizi et al. | |
| 5,957,949 A | 9/1999 | Leonhardt et al. | |
| 5,976,174 A | 11/1999 | Ruiz | |
| 5,984,965 A | 11/1999 | Knapp et al. | |
| 6,007,575 A | 12/1999 | Samuels | |
| 6,009,614 A | 1/2000 | Morales | |
| 6,020,380 A | 2/2000 | Killian | |
| 6,022,312 A | 2/2000 | Chaussy et al. | |
| 6,027,525 A | 2/2000 | Suh et al. | |
| 6,033,359 A * | 3/2000 | Doi | 600/117 |
| 6,042,554 A * | 3/2000 | Rosenman et al. | 623/2.11 |
| 6,051,022 A | 4/2000 | Cai et al. | |
| 6,068,635 A | 5/2000 | Gianotti | |
| 6,068,638 A | 5/2000 | Makower | |
| 6,077,291 A | 6/2000 | Das | |
| 6,083,255 A | 7/2000 | Laufer et al. | |
| 6,123,663 A | 9/2000 | Rebuffat | |
| 6,135,729 A | 10/2000 | Aber | |
| 6,135,991 A | 10/2000 | Muni et al. | |
| 6,141,855 A | 11/2000 | Morales | |
| 6,143,021 A | 11/2000 | Staehle | |
| 6,162,245 A | 12/2000 | Jayaraman | |
| 6,168,614 B1 | 1/2001 | Andersen et al. | |
| 6,174,323 B1 | 1/2001 | Biggs et al. | |
| 6,183,520 B1 | 2/2001 | Pintauro et al. | |
| 6,200,333 B1 | 3/2001 | Laufer | |
| 6,206,918 B1 | 3/2001 | Campbell et al. | |
| 6,234,996 B1 | 5/2001 | Bagaoisan et al. | |
| 6,240,615 B1 | 6/2001 | Kimes et al. | |
| 6,245,102 B1 | 6/2001 | Jayaraman | |
| 6,258,100 B1 | 7/2001 | Alferness et al. | |
| 6,270,527 B1 | 8/2001 | Campbell et al. | |
| 6,287,290 B1 | 9/2001 | Perkins et al. | |
| 6,293,951 B1 | 9/2001 | Alferness et al. | |
| 6,302,893 B1 | 10/2001 | Limon et al. | |
| 6,312,407 B1 | 11/2001 | Zadno-Azizi et al. | |
| 6,325,777 B1 | 12/2001 | Zadno-Azizi et al. | |
| 6,325,778 B1 | 12/2001 | Zadno-Azizi et al. | |
| 6,327,772 B1 | 12/2001 | Zadno-Azizi et al. | |
| 6,328,689 B1 | 12/2001 | Gonzalez | |
| 6,350,278 B1 | 2/2002 | Lenker et al. | |
| 6,355,014 B1 | 3/2002 | Zadno-Azizi et al. | |
| 6,398,775 B1 | 6/2002 | Perkins et al. | |
| 6,402,754 B1 | 6/2002 | Gonzalez | |
| 6,416,554 B1 | 7/2002 | Alferness et al. | |
| 6,450,976 B2 * | 9/2002 | Korotko et al. | 600/587 |
| 6,458,076 B1 | 10/2002 | Pruitt | |
| 6,485,407 B2 | 11/2002 | Alferness et al. | |
| 6,491,706 B1 | 12/2002 | Alferness et al. | |
| 6,493,589 B1 | 12/2002 | Medhkour et al. | |
| 6,510,846 B1 | 1/2003 | O'Rourke | |
| 6,524,259 B2 * | 2/2003 | Baxter-Jones et al. | 600/591 |
| 6,527,761 B1 | 3/2003 | Soltesz et al. | |
| 6,632,243 B1 | 10/2003 | Zadno-Azizi et al. | |
| 6,679,264 B1 | 1/2004 | Deem et al. | |
| 6,694,979 B2 | 2/2004 | Deem et al. | |
| 6,802,846 B2 | 10/2004 | Hauschild et al. | |
| 6,840,243 B2 | 1/2005 | Deem et al. | |
| 6,878,141 B1 | 4/2005 | Perkins et al. | |
| 6,901,927 B2 | 6/2005 | Deem et al. | |
| 6,904,909 B2 | 6/2005 | Andreas et al. | |
| 6,941,950 B2 | 9/2005 | Wilson et al. | |
| 2001/0025132 A1 | 9/2001 | Alferness et al. | |
| 2001/0027323 A1 | 10/2001 | Sullivan, III et al. | |
| 2001/0037808 A1 | 11/2001 | Deem et al. | |
| 2001/0041906 A1 | 11/2001 | Gonzalez | |
| 2001/0051799 A1 | 12/2001 | Ingenito | |
| 2001/0052344 A1 | 12/2001 | Doshi | |
| 2001/0056274 A1 | 12/2001 | Perkins et al. | |
| 2002/0007831 A1 | 1/2002 | Davenport et al. | |
| 2002/0026233 A1 | 2/2002 | Shaknovich | |
| 2002/0062120 A1 | 5/2002 | Perkins et al. | |
| 2002/0077593 A1 | 6/2002 | Perkins et al. | |
| 2002/0077696 A1 | 6/2002 | Zadno-Azizi et al. | |
| 2002/0087153 A1 | 7/2002 | Roschak et al. | |
| 2002/0095209 A1 | 7/2002 | Zadno-Azizi et al. | |
| 2002/0111619 A1 | 8/2002 | Keast et al. | |
| 2002/0111620 A1 | 8/2002 | Cooper et al. | |
| 2002/0112729 A1 | 8/2002 | DeVore et al. | |
| 2002/0138135 A1 | 9/2002 | Duerig et al. | |
| 2003/0018327 A1 | 1/2003 | Truckai et al. | |
| 2003/0018344 A1 | 1/2003 | Kaji et al. | |
| 2003/0050648 A1 | 3/2003 | Alferness et al. | |

| | | | | | | |
|---|---|---|---|---|---|---|
| 2003/0070682 | A1 | 4/2003 | Wilson et al. | WO | 01/03642 | 1/2001 |
| 2003/0070683 | A1* | 4/2003 | Deem et al. ............ 128/207.16 | WO | 01/05334 | 1/2001 |
| 2003/0075169 | A1 | 4/2003 | Deem et al. | WO | 01/10313 | 2/2001 |
| 2003/0075170 | A1 | 4/2003 | Deem et al. | WO | 01/10314 | 2/2001 |
| 2003/0083671 | A1 | 5/2003 | Rimbaugh et al. | WO | 01/12104 | 2/2001 |
| 2003/0127090 | A1 | 7/2003 | Gifford et al. | WO | 01/13839 | 3/2001 |
| 2003/0164168 | A1 | 9/2003 | Shaw | WO | 01/13908 | 3/2001 |
| 2003/0181922 | A1 | 9/2003 | Alferness | WO | 01/28433 | 4/2001 |
| 2003/0183235 | A1 | 10/2003 | Rimbaugh et al. | WO | 01/45590 | 6/2001 |
| 2003/0192550 | A1 | 10/2003 | Deem et al. | WO | 01/49213 | 7/2001 |
| 2003/0192551 | A1 | 10/2003 | Deem et al. | WO | 01/54585 | 8/2001 |
| 2003/0199972 | A1 | 10/2003 | Zadno-Azizi et al. | WO | 01/54625 | 8/2001 |
| 2003/0212452 | A1 | 11/2003 | Zadno-Azizi et al. | WO | 01/54685 | 8/2001 |
| 2003/0228344 | A1 | 12/2003 | Fields et al. | WO | 01/66190 | 9/2001 |
| 2004/0016435 | A1 | 1/2004 | Deem et al. | WO | 01/74271 | 10/2001 |
| 2004/0039250 | A1 | 2/2004 | Tholfsen et al. | WO | 01/87170 | 11/2001 |
| 2004/0055606 | A1 | 3/2004 | Hendricksen et al. | WO | 01/89366 | 11/2001 |
| 2004/0060563 | A1 | 4/2004 | Rapacki et al. | WO | 01/95786 | 12/2001 |
| 2004/0074491 | A1 | 4/2004 | Hendricksen et al. | WO | 02/05884 | 1/2002 |
| 2004/0089306 | A1 | 5/2004 | Hundertmark et al. | WO | 02/22072 | 3/2002 |
| 2004/0134487 | A1 | 7/2004 | Deem et al. | WO | 02/32333 | 4/2002 |
| 2004/0148035 | A1 | 7/2004 | Barrett et al. | WO | 02/34322 | 5/2002 |
| 2004/0154621 | A1 | 8/2004 | Deem et al. | WO | 02/38038 | 5/2002 |
| 2004/0211434 | A1 | 10/2004 | Loomas et al. | WO | 02/47575 | 6/2002 |
| 2005/0016530 | A1 | 1/2005 | McCutcheon et al. | WO | 02/056794 | 7/2002 |
| 2005/0051163 | A1 | 3/2005 | Deem et al. | WO | 02/064045 | 8/2002 |
| 2005/0066974 | A1 | 3/2005 | Fields et al. | WO | 02/064190 | 8/2002 |
| 2005/0087137 | A1 | 4/2005 | Park et al. | WO | 02/069823 | 9/2002 |
| 2005/0145253 | A1 | 7/2005 | Wilson et al. | WO | 02/094087 | 11/2002 |
| 2005/0161048 | A1 | 7/2005 | Rapacki et al. | WO | 03/022124 | 3/2003 |
| 2005/0166925 | A1 | 8/2005 | Wilson et al. | WO | 03/079944 | 10/2003 |
| 2005/0178389 | A1 | 8/2005 | Shaw et al. | WO | 03/088912 | 10/2003 |
| 2005/0196344 | A1 | 9/2005 | McCutcheon et al. | WO | 2004/049974 | 6/2004 |
| 2006/0020347 | A1 | 1/2006 | Barrett et al. | | | |

FOREIGN PATENT DOCUMENTS

| | | |
|---|---|---|
| EP | 0 346 564 | 12/1989 |
| EP | 0 621 015 B1 | 10/1994 |
| EP | 1 078 601 A2 | 2/2001 |
| EP | 1 151 729 A1 | 11/2001 |
| GB | 2324729 | 4/1998 |
| GB | 2 373 445 | 9/2002 |
| JP | 2000292108 A * | 10/2000 |
| RU | 2140211 | 10/1999 |
| SU | 852321 | 7/1981 |
| SU | 1371700 | 2/1988 |
| SU | 1593651 | 9/1990 |
| WO | 94/26175 | 11/1994 |
| WO | 95/32018 | 11/1995 |
| WO | 96/34582 | 11/1996 |
| WO | 96/39960 | 12/1996 |
| WO | 97/44085 | 11/1997 |
| WO | 98/00840 | 1/1998 |
| WO | 98/19633 | 5/1998 |
| WO | 98/39047 | 9/1998 |
| WO | 98/44854 A1 | 10/1998 |
| WO | 98/48706 | 11/1998 |
| WO | 99/01076 | 1/1999 |
| WO | 99/13801 | 3/1999 |
| WO | 99/26692 | 6/1999 |
| WO | 99/32040 | 7/1999 |
| WO | 99/42059 | 8/1999 |
| WO | 99/42161 | 8/1999 |
| WO | 99/64109 A1 | 12/1999 |
| WO | 00/15149 | 3/2000 |
| WO | 00/18330 | 4/2000 |
| WO | 00/42950 | 7/2000 |
| WO | 00/51510 | 9/2000 |
| WO | 00/62699 | 10/2000 |
| WO | 00/78386 | 12/2000 |
| WO | 00/78407 | 12/2000 |
| WO | 01/02042 | 1/2001 |

OTHER PUBLICATIONS

Ogoshi Yasushi, Machine English translation of JP, 2000-292108, and A [Full Contents] by JPO and INPIT, Oct. 20, 2000; Translated: Jun. 5, 2010; entire document.*

AI Jishi et al., "Selective Bronchial Occlusion for Treatment of Bullous Interstitial Emphysema and Bronchopleural Fistula." *J. of Pediatric Surgery*, 29:1545-1547, 1994.

Article: "Autocath® 100—Nonsurgical, Intraurethral Bladder Control Device for Incontinent and Retentive Women—Dr. Kulisz's Development".

Certified English Translation of German patent G 92 05 797.7, published Jul. 30, 1993, entitled "Self-expanding mesh basket used to occlude human hollow organs".

Certified English Translation of USSR patent 852321, published Aug. 7, 1981, entitled "A Method of Treatment of Acute Purulent Diseases of the Lungs and Pleura in Children".

Derwent citing Russian Patent No. RU 2140211, published Oct. 27, 1999, for: "Method of surgical treatment of patients with pathology of respiratory organs complicated with pulmonary hemorrhages".

Derwent citing Soviet Union Patent No. SU 852-321, published Jul. 8, 1981, for: "Treatment for acute pulmonary and pleural disease in children—by pneumo-abcessotomy simultaneous with occlusion of affected lung part".

Derwent# 007607249 WPI Acc. No. 1988-241181/198834 (citing Russian Application No. SU4026409, published Feb. 21, 1986), Russian Patent No. SU 1371700.

Derwent# 008650867 WPI Acc. No. 1991-154896/199121 (citing Russian Application No. SU4280143, published Jul. 7, 1987), Russian Patent No. SU 1593651.

Harris et al., "The Experimental Production in Dogs of Emphysema with Associated Asthmatic Syndrome by Means of an Intratracheal Ball Valve", *J. Lab. Clini. Med.*, 9(iv):75-88, 1919.

Lewis et al., "Pulmonary Interstitial Emphysema: Selective Broncial Occlusion with a Swan-Ganz Catheter", *Archives of Disease in Childhood*, 63:313-315, 1988.

Mathew et al., "Selective bronchial obstruction for treatment of bullous interstitial emphysema." *J. of Ped.*, 96:475-477, 1980.

Okada et al., "Emergent Bronchofiberoptic Bronchial Occlusion for Intractable Pneumothorax with Severe Emphysema", *The Jap. J. of Thor. And Cardio. Sur.*, 46:1078-1081, 1998.

Puhakka et al., "Acute Bronchial Obstruction: An Experimental Rabbit Model Study", *Int. J. of Pediatric Otorhinolaryngology*, 18:107-118, 1989.

Snider et al., The Definition of Emphysema: Report of the National Heart Lung and Blood Institute, Division of Lung Diseases Workshop, *Am. Rev. Respir. Dis.*, 132:182-185, 1985.

Woodring et al., "Pneumothorax ex Vacuo", *Chest*, 100:1102-1124, 1996.

* cited by examiner

DELIVERY METHODS AND DEVICES FOR IMPLANTABLE BRONCHIAL ISOLATION DEVICES

REFERENCE TO PRIORITY DOCUMENT

This application is a continuation-in-part of co-pending U.S. patent application Ser. No. 10/723,273, entitled "Delivery Methods and Devices For Implantable Bronchial Isolation Devices", filed Nov. 25, 2003, which claims priority of U.S. Provisional Patent Application Ser. No. 60/429,902 entitled "Implantable Bronchial Isolation Devices", filed Nov. 27, 2002. Priority of the aforementioned filing dates is hereby claimed, and the disclosures of the aforementioned patent applications are hereby incorporated by reference in their entirety.

BACKGROUND OF THE INVENTION

1. Field of the Invention

This invention relates generally to methods and devices for use in performing pulmonary procedures and, more particularly, to devices and procedures for treating lung diseases.

2. Description of the Related Art

Certain pulmonary diseases, such as emphysema, reduce the ability of one or both lungs to fully expel air during the exhalation phase of the breathing cycle. Such diseases are accompanied by chronic or recurrent obstruction to air flow within the lung. One of the effects of such diseases is that the diseased lung tissue is less elastic than healthy lung tissue, which is one factor that prevents full exhalation of air. During breathing, the diseased portion of the lung does not fully recoil due to the diseased (e.g., emphysematic) lung tissue being less elastic than healthy tissue. Consequently, the diseased lung tissue exerts a relatively low driving force, which results in the diseased lung expelling less air volume than a healthy lung.

The problem is further compounded by the diseased, less elastic tissue that surrounds the very narrow airways that lead to the alveoli, which are the air sacs where oxygen-carbon dioxide exchange occurs. The diseased tissue has less tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange.

In addition, hyper-expanded, diseased lung tissue occupies more of the pleural space than healthy lung tissue. In most cases, a portion of the lung is diseased while the remaining part is relatively healthy and, therefore, still able to efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent healthy tissue.

Lung reduction surgery is a conventional method of treating emphysema. However, such a conventional surgical approach is relatively traumatic and invasive, and, like most surgical procedures, is not a viable option for all patients.

Some recently proposed treatments for emphysema or other lung ailments include the use of devices that isolate a diseased region of the lung in order to modify the air flow to the targeted lung region or to achieve volume reduction or collapse of the targeted lung region. According to such treatments, one or more bronchial isolation devices are implanted in airways feeding the targeted region of the lung. The bronchial isolation device regulates fluid flow through the bronchial passageway in which the bronchial isolation device is implanted. The bronchial isolation devices can be, for example, one-way valves that allow flow in the exhalation direction only, occluders or plugs that prevent flow in either direction, or two-way valves that control flow in both directions.

The following references describe exemplary bronchial isolation devices: U.S. Pat. No. 5,954,766 entitled "Body Fluid Flow Control Device"; U.S. patent application Ser. No. 09/797,910, entitled "Methods and Devices for Use in Performing Pulmonary Procedures"; and U.S. patent application Ser. No. 10/270,792, entitled "Bronchial Flow Control Devices and Methods of Use". The foregoing references are all incorporated by reference in their entirety and are all assigned to Emphasys Medical, Inc., the assignee of the instant application.

The bronchial isolation device can be implanted in a target bronchial passageway using a delivery catheter that is placed through the trachea (via the mouth or the nasal cavities) and to the target location in the bronchial passageway. It would be advantageous to develop improved methods and devices for delivering bronchial isolation devices into the lung of a patient.

SUMMARY

Disclosed is a device for sizing an inside diameter of a lung passageway. In one aspect, the sizing device comprises an elongate shaft configured for positioning in the lung passageway and a sizing element at the distal end of the shaft. The sizing element defines a range of transverse dimensions that correspond to a range of transverse dimensions suitable for use with a predetermined set of bronchial isolation devices. The device is used to determine the suitability of a bronchial isolation device for use in the lung passageway prior to using a separate delivery catheter to deliver the bronchial isolation device into the lung passageway.

In another aspect, there is disclosed a device for sizing an inside diameter of a lung passageway. The device comprises an elongate shaft configured for positioning in the lung passageway and a sizing element disposed on a distal end of the shaft. The sizing element provides an indication as to the size of the lung passageway for selection of a bronchial isolation device to be inserted into the lung passageway.

Other features and advantages of the present invention should be apparent from the following description of various embodiments, which illustrate, by way of example, the principles of the invention.

DETAILED DESCRIPTION

Unless defined otherwise, all technical and scientific terms used herein have the same meaning as is commonly understood by one of skill in the art to which the invention(s) belong. It should be noted that the various devices and methods disclosed herein are not limited to the treatment of emphysema, and may be used for various other lung diseases.

Disclosed are various devices and methods for delivering one or more bronchial isolation devices (which are sometimes referred to herein as flow control devices) to a location in a bronchial passageway. The bronchial isolation device is delivered to a target location in the bronchial passageway by mounting the bronchial isolation device in a housing at the distal end of a delivery catheter and then inserting the delivery catheter into the bronchial passageway. Once the housing is positioned at a target location in the bronchial passageway, the bronchial isolation device is ejected from the housing and deployed within the passageway. In the example shown in FIG. 1, the distal end of the delivery catheter 110 is inserted into the patient's mouth or nose, through the trachea, and down to a target location in the bronchial passageway 517. For clarity of illustration, FIG. 1 does not show the housing in which the device is contained.

The following references describe exemplary bronchial isolation devices and delivery devices: U.S. Pat. No. 5,954,766 entitled "Body Fluid Flow Control Device"; U.S. patent application Ser. No. 09/797,910, entitled "Methods and Devices for Use in Performing Pulmonary Procedures"; U.S. patent application Ser. No. 10/270,792, entitled "Bronchial Flow Control Devices and Methods of Use"; and U.S. patent application Ser. No. 10/448,154, entitled "Guidewire Delivery of Implantable Bronchial Isolation Devices in Accordance with Lung Treatment". The foregoing references are all incorporated by reference in their entirety and are all assigned to Emphasys Medical, Inc., the assignee of the instant application.

Exemplary Lung Regions

Throughout this disclosure, reference is made to the term "lung region". As used herein, the term "lung region" refers to a defined division or portion of a lung. For purposes of example, lung regions are described herein with reference to human lungs, wherein some exemplary lung regions include lung lobes and lung segments. Thus, the term "lung region" as used herein can refer, for example, to a lung lobe or a lung segment. Such nomenclature conform to nomenclature for portions of the lungs that are known to those skilled in the art. However, it should be appreciated that the term "lung region" does not necessarily refer to a lung lobe or a lung segment, but can refer to some other defined division or portion of a human or non-human lung.

Figure 2:
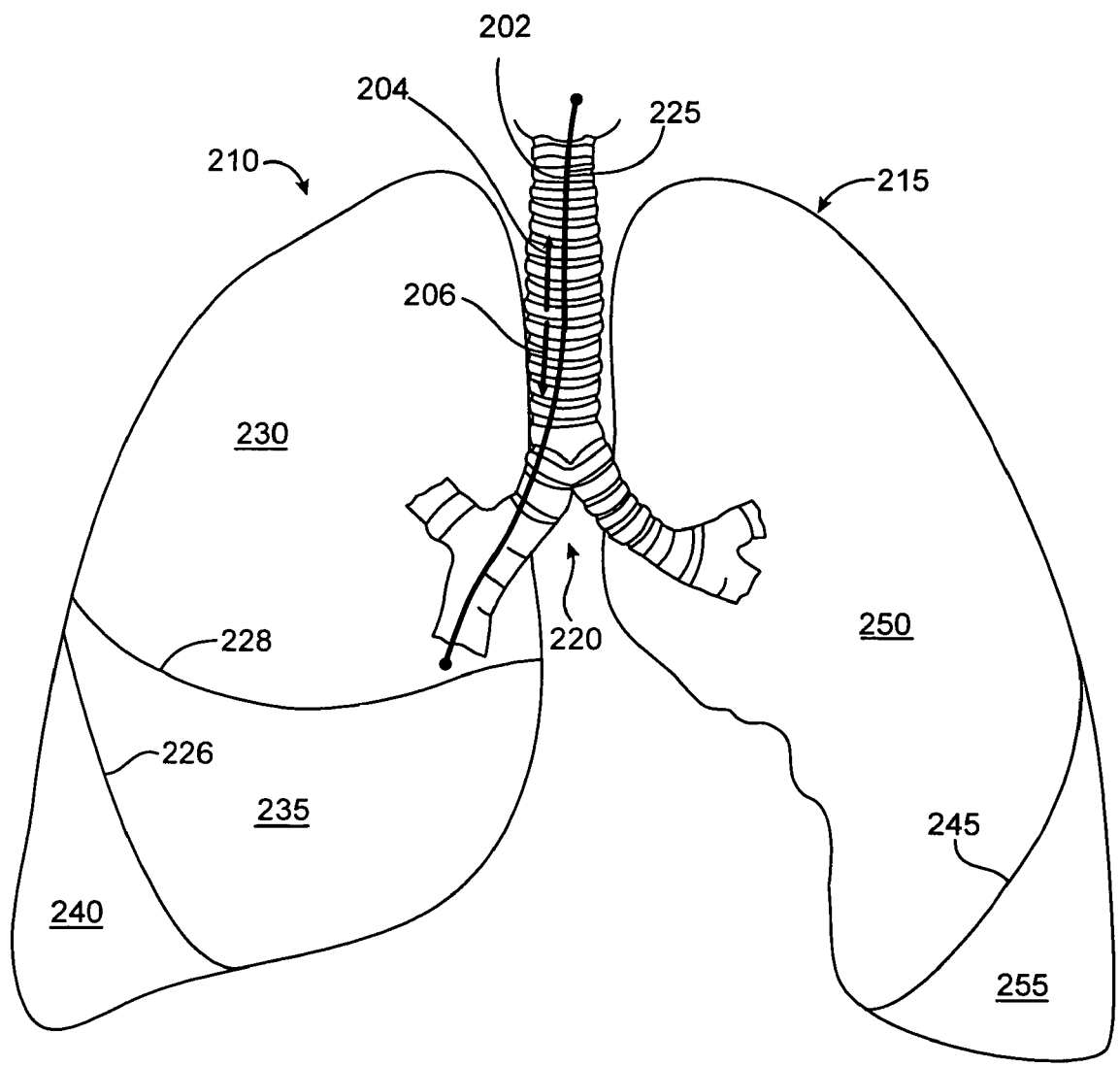
FIG. 2 illustrates an anterior view of a pair of human lungs and a bronchial tree.

FIG. 2 shows an anterior view of a pair of human lungs 210, 215 and a bronchial tree 220 that provides a fluid pathway into and out of the lungs 210, 215 from a trachea 225, as will be known to those skilled in the art. As used herein, the term "fluid" can refer to a gas, a liquid, or a combination of gas(es) and liquid(s). For clarity of illustration, FIG. 2 shows only a portion of the bronchial tree 220, which is described in more detail below with reference to FIG. 5.

Throughout this description, certain terms are used that refer to relative directions or locations along a path defined from an entryway into the patient's body (e.g., the mouth or nose) to the patient's lungs. The path of airflow into the lungs generally begins at the patient's mouth or nose, travels through the trachea into one or more bronchial passageways, and terminates at some point in the patient's lungs. For example, FIG. 2 shows a path 202 that travels through the trachea 225 and through a bronchial passageway into a location in the right lung 210. The term "proximal direction" refers to the direction along such a path 202 that points toward the patient's mouth or nose and away from the patient's lungs. In other words, the proximal direction is generally the same as the expiration direction when the patient breathes. The arrow 204 in FIG. 2 points in the proximal or expiratory direction. The term "distal direction" refers to the direction along such a path 202 that points toward the patient's lung and away from the mouth or nose. The distal direction is generally the same as the inhalation or inspiratory direction when the patient breathes. The arrow 206 in FIG. 2 points in the distal or inhalation direction.

The lungs include a right lung 210 and a left lung 215. The right lung 210 includes lung regions comprised of three lobes, including a right upper lobe 230, a right middle lobe 235, and a right lower lobe 240. The lobes 230, 235, 240 are separated by two interlobar fissures, including a right oblique fissure 226 and a right transverse fissure 228. The right oblique fissure 226 separates the right lower lobe 240 from the right upper lobe 230 and from the right middle lobe 235. The right transverse fissure 228 separates the right upper lobe 230 from the right middle lobe 235.

As shown in FIG. 2, the left lung 215 includes lung regions comprised of two lobes, including the left upper lobe 250 and the left lower lobe 255. An interlobar fissure comprised of a left oblique fissure 245 of the left lung 215 separates the left upper lobe 250 from the left lower lobe 255. The lobes 230, 235, 240, 250, 255 are directly supplied air via respective lobar bronchi, as described in detail below.

Figure 3:
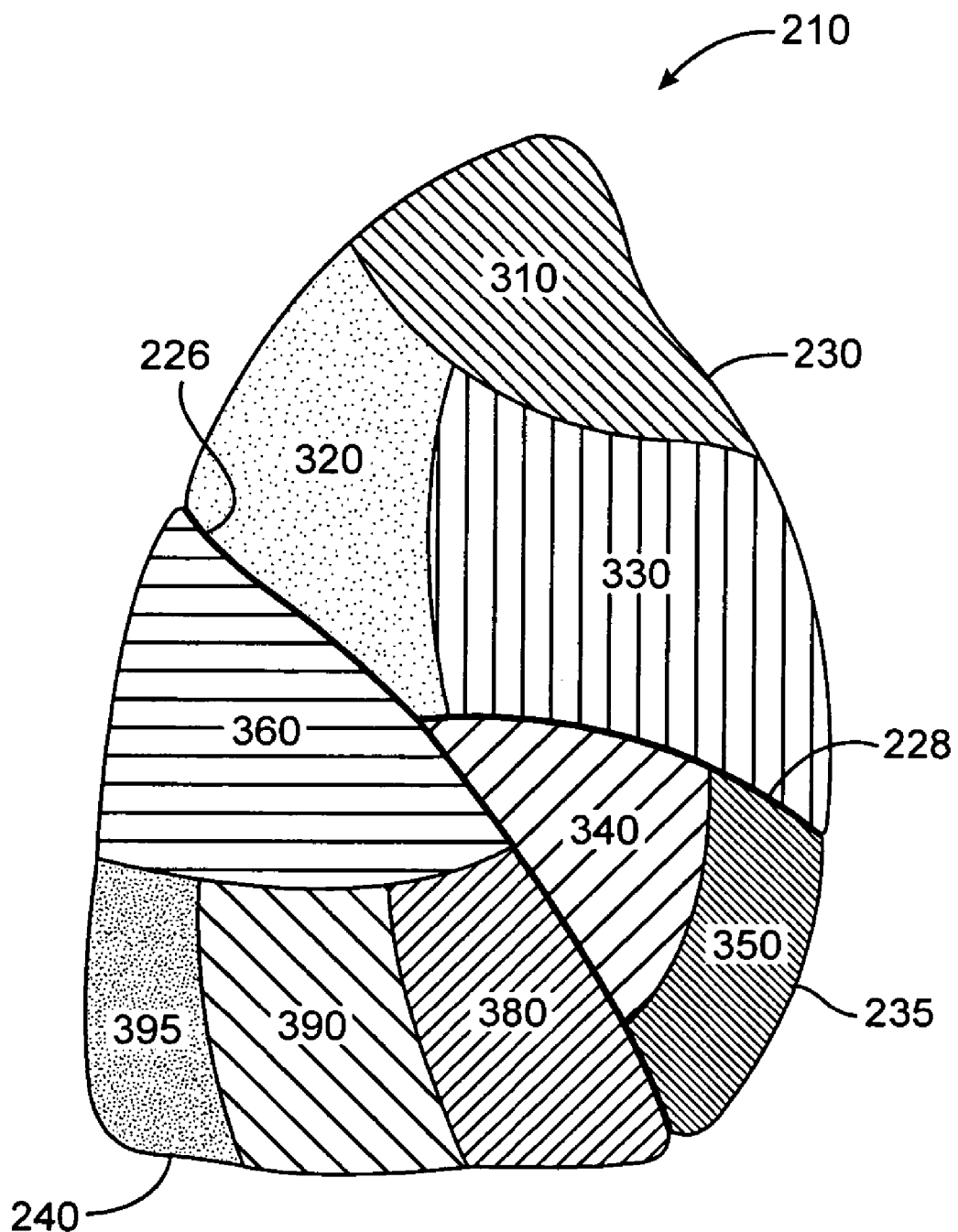
FIG. 3 illustrates a lateral view of the right lung.

FIG. 3 is a lateral view of the right lung 210. The right lung 210 is subdivided into lung regions comprised of a plurality of bronchopulmonary segments. Each bronchopulmonary segment is directly supplied air by a corresponding segmental tertiary bronchus, as described below. The bronchopulmonary segments of the right lung 210 include a right apical segment 310, a right posterior segment 320, and a right anterior segment 330, all of which are disposed in the right upper lobe 230. The right lung bronchopulmonary segments further include a right lateral segment 340 and a right medial segment 350, which are disposed in the right middle lobe 235. The right lower lobe 240 includes bronchopulmonary segments comprised of a right superior segment 360, a right medial basal segment (which cannot be seen from the lateral view and is not shown in FIG. 3), a right anterior basal segment 380, a right lateral basal segment 390, and a right posterior basal segment 395.

Figure 4:
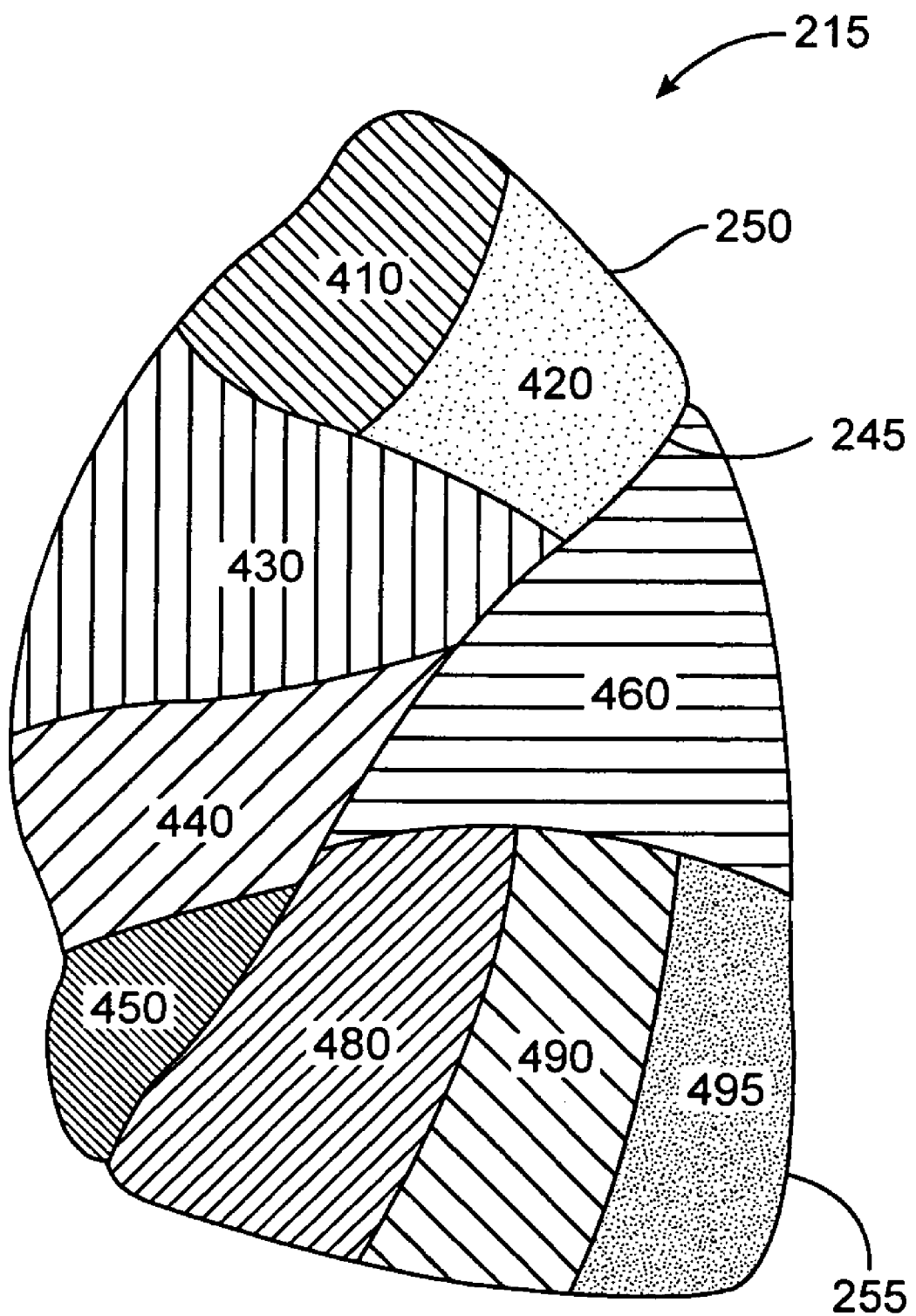
FIG. 4 illustrates a lateral view of the left lung.

FIG. 4 shows a lateral view of the left lung 215, which is subdivided into, lung regions comprised of a plurality of bronchopulmonary segments. The bronchopulmonary segments include a left apical segment 410, a left posterior segment 420, a left anterior segment 430, a left superior segment 440, and a left inferior segment 450, which are disposed in the left lung upper lobe 250. The lower lobe 255 of the left lung 215 includes bronchopulmonary segments comprised of a left superior segment 460, a left medial basal segment (which cannot be seen from the lateral view and is not shown in FIG. 4), a left anterior basal segment 480, a left lateral basal segment 490, and a left posterior basal segment 495.

Figure 5:
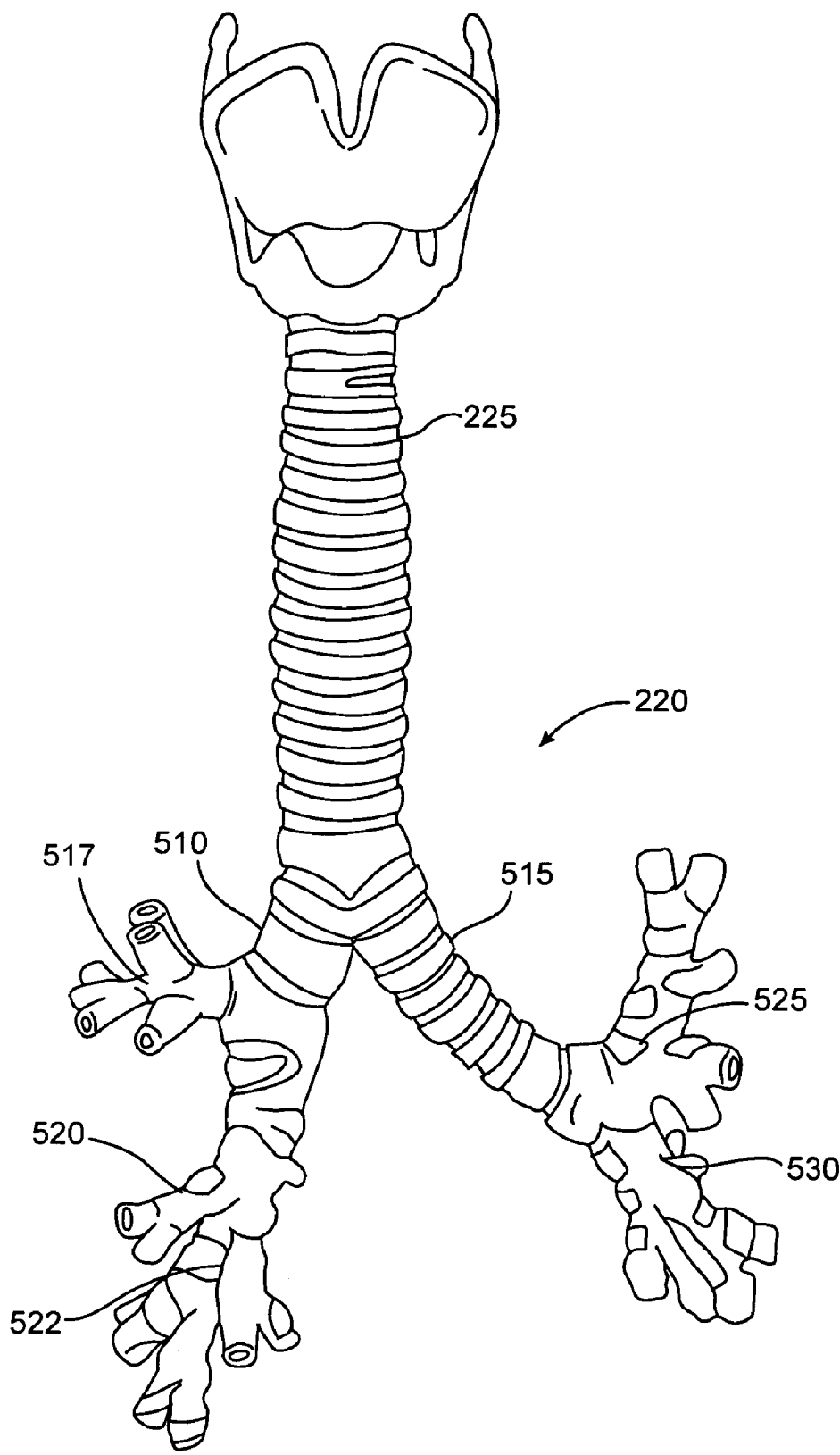
FIG. 5 illustrates an anterior view of the trachea and a portion of the bronchial tree.

FIG. 5 shows an anterior view of the trachea 325 and a portion of the bronchial tree 220, which includes a network of bronchial passageways, as described below. The trachea 225 divides at a lower end into two bronchial passageways comprised of primary bronchi, including a right primary bronchus 510 that provides direct air flow to the right lung 210, and a left primary bronchus 515 that provides direct air flow to the left lung 215. Each primary bronchus 510, 515 divides into a next generation of bronchial passageways comprised of a plurality of lobar bronchi. The right primary bronchus 510 divides into a right upper lobar bronchus 517, a right middle lobar bronchus 520, and a right lower lobar bronchus 422. The left primary bronchus 415 divides into a left upper lobar bronchus 525 and a left lower lobar bronchus 530. Each lobar bronchus 517, 520, 522, 525, 530 directly feeds fluid to a respective lung lobe, as indicated by the respective names of the lobar bronchi. The lobar bronchi each divide into yet another generation of bronchial passageways comprised of segmental bronchi, which provide air flow to the bronchopulmonary segments discussed above.

As is known to those skilled in the art, a bronchial passageway defines an internal lumen through which fluid can flow to and from a lung or lung region. The diameter of the internal lumen for a specific bronchial passageway can vary based on the bronchial passageway's location in the bronchial tree (such as whether the bronchial passageway is a lobar bronchus or a segmental bronchus) and can also vary from patient to patient. However, the internal diameter of a bronchial passageway is generally in the range of 3 millimeters (mm) to 10 mm, although the internal diameter of a bronchial passageway can be outside of this range. For example, a bronchial passageway can have an internal diameter of well below 1 mm at locations deep within the lung. The internal diameter can also vary from inhalation to exhalation as the diameter increases during inhalation as the lungs expand, and decreases during exhalation as the lungs contract.

Bronchial Isolation Device Delivery System

As discussed above, the bronchial isolation device is deployed in the bronchial passageway using a delivery catheter 110, which is inserted into the bronchial passageway through the patient's trachea. In one embodiment, the delivery catheter 110 is inserted directly into the trachea and bronchial passageway. In another embodiment, shown in FIG. 1, a bronchoscope 120 assists in the insertion of the delivery catheter 110 through the trachea and into the bronchial passageway. The method that uses the bronchoscope 120 is referred to as the "transcopic" method. According to the transcopic method, the delivery catheter 110 is inserted into the working channel of the bronchoscope 120, which is deployed to the bronchial passageway 517 either before or after the delivery catheter has been inserted into the bronchoscope 120.

Figure 1:
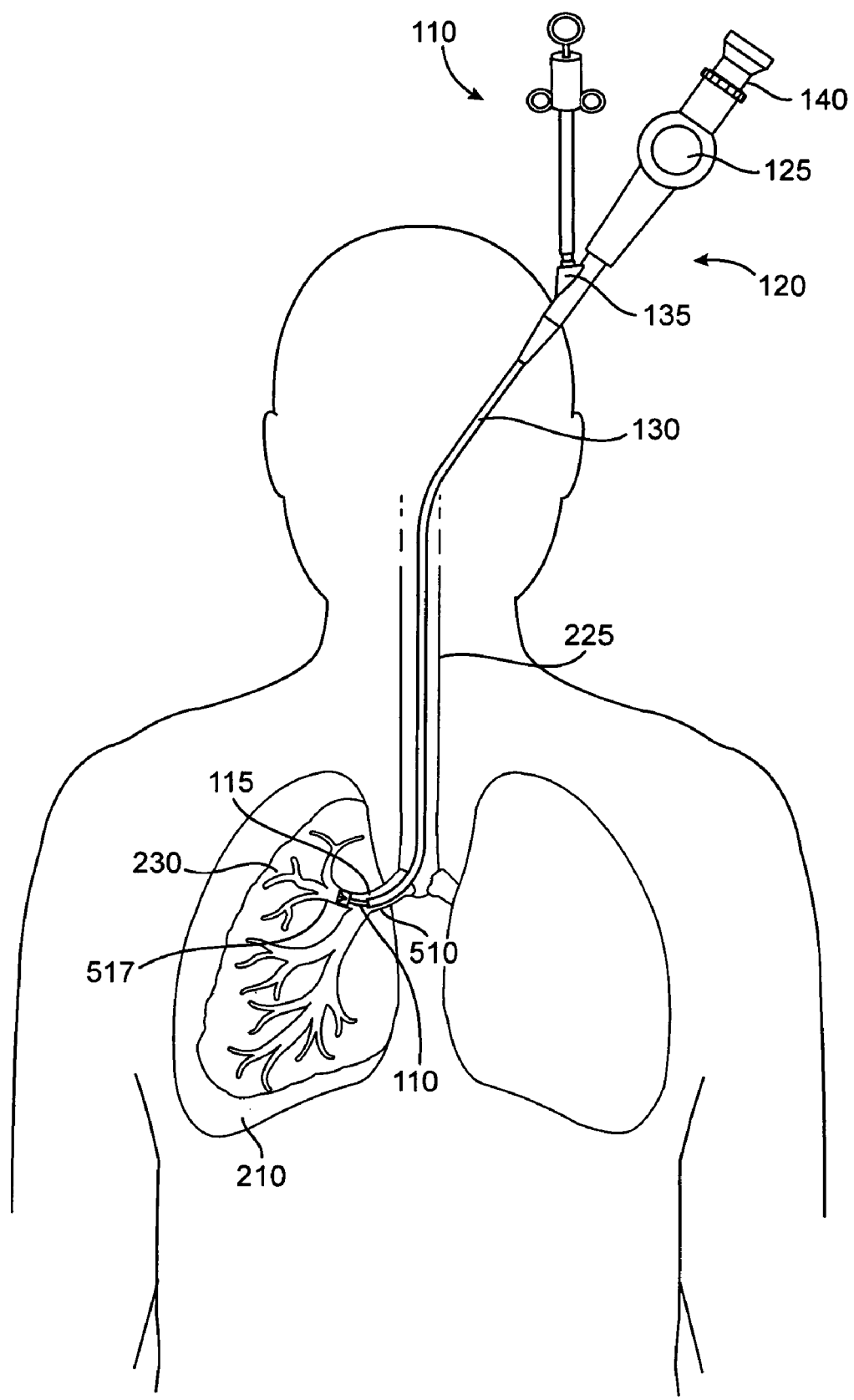
FIG. 1 shows an anterior view of a pair of human lungs and a bronchial tree with a bronchial isolation device implanted in a bronchial passageway to bronchially isolate a region of the lung.
Figure 6:
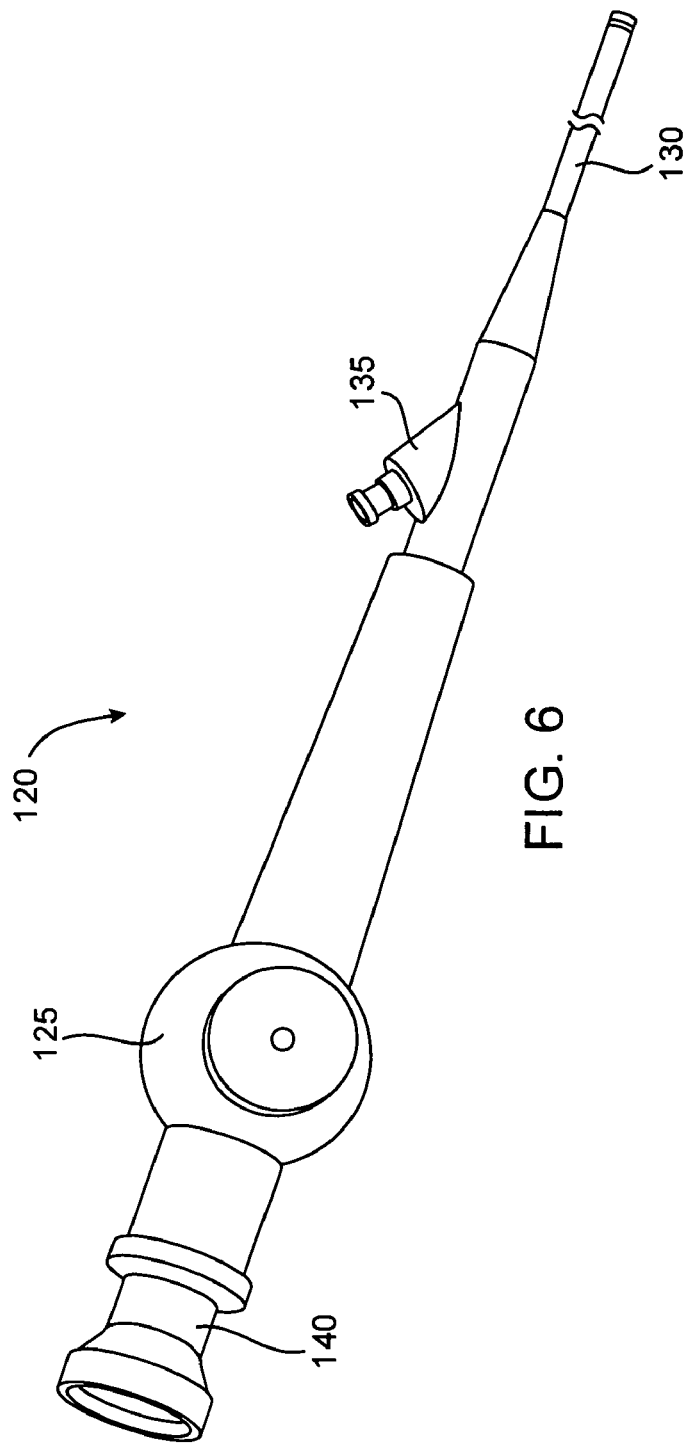
FIG. 6 shows a perspective view of a bronchoscope.

As shown in FIGS. 1 and 6, in an exemplary embodiment the bronchoscope 120 has a steering mechanism 125, a delivery shaft 130, a working channel entry port 135, and a visualization eyepiece 140. FIG. 1 shows the bronchoscope 120 positioned with its distal end at the right primary bronchus 510. The delivery catheter 110 is positioned within the bronchoscope 120 such that the delivery catheter's distal end and the attached bronchial isolation device 115 protrude outward from the distal end of the bronchoscope 120, as shown in FIG. 1.

Figure 7:
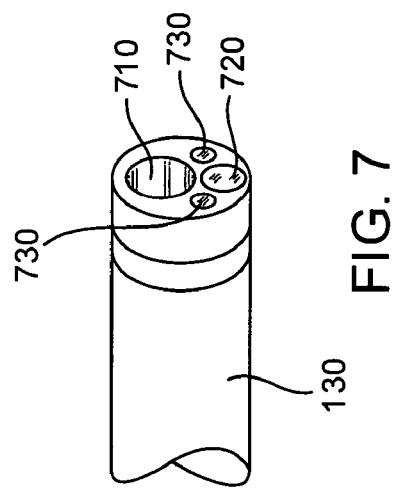
FIG. 7 shows an enlarged view of a distal region of a bronchoscope.

FIG. 6 shows an enlarged view of the bronchoscope 120, including the steering mechanism 125, delivery shaft 130, working channel entry port 135, and visualization eyepiece 140. In addition, the bronchoscope can also include a fiber optic bundle mounted inside the length of the bronchoscope for transferring an image from the distal end to the eyepiece 140. In one embodiment, the bronchoscope also includes a camera or charge-coupled device (CCD) for generating an image of the bronchial tree. FIG. 7 shows an enlarged view of the distal portion of the bronchoscope 120. A working channel 710 (sometimes referred to as a biopsy channel) extends through the delivery shaft 130 and communicates with the entry port 135 (shown in FIG. 6) at the proximal end of the bronchoscope 120. The working channel 710 can sometimes be formed by an extruded plastic tube inside the body of the bronchoscope 120. The bronchoscope 120 can also include various other channels, such as a visualization channel 720 that communicates with the eyepiece 140 and one or more illumination channels 730. It should be appreciated that the bronchoscope can have a variety of configurations and is not limited to the embodiment shown in the figures. For example, in an alternative embodiment, the working channel 710 may be formed of a flexible material and temporarily or permanently attached to the outside of the delivery shaft 130.

Figure 8:
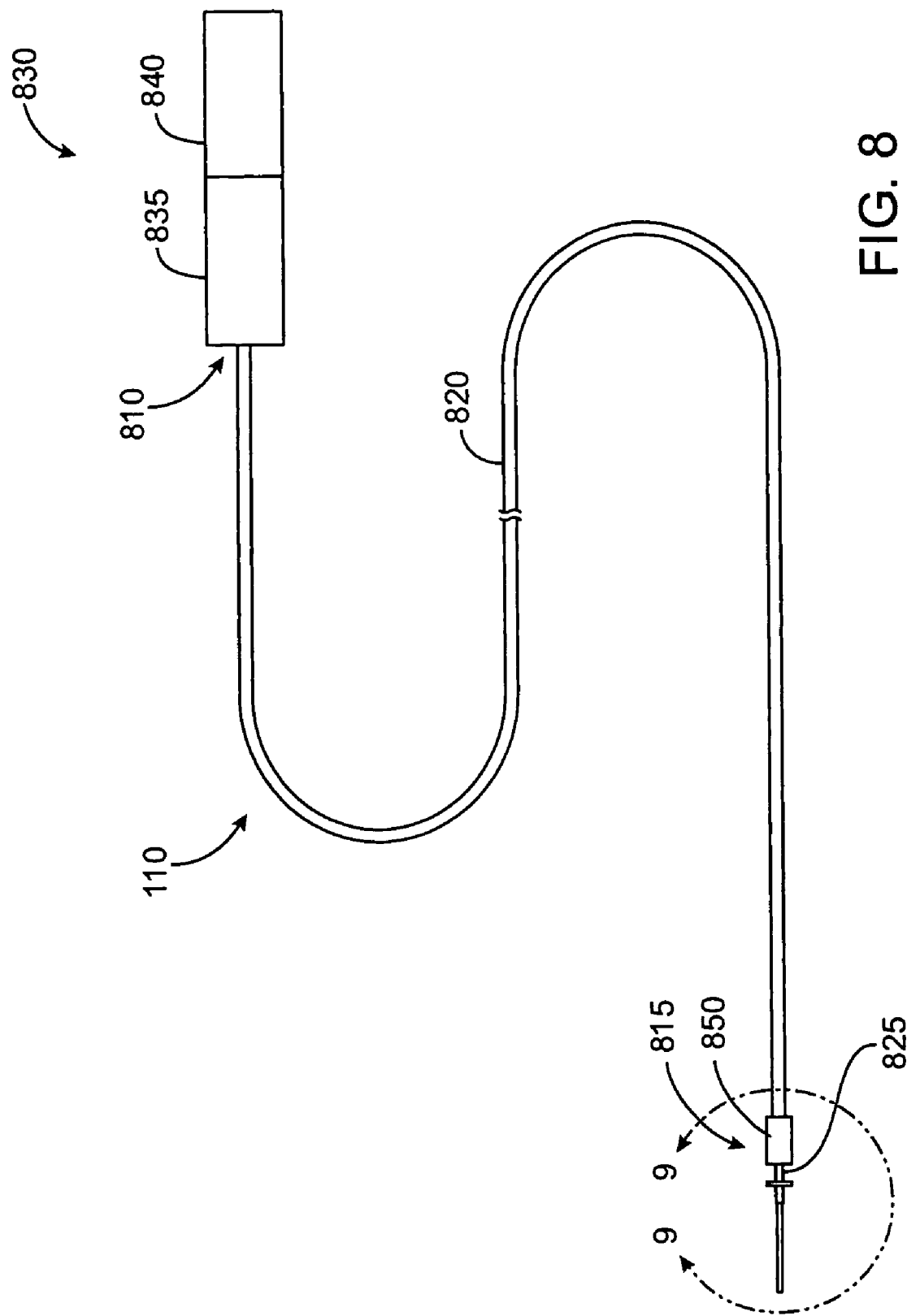
FIG. 8 shows a delivery catheter for delivering a bronchial isolation device to a target location in a body passageway.

FIG. 8 shows one embodiment of the delivery catheter 110 for delivering and deploying the bronchial isolation device 115 to a target location in a bronchial passageway. The delivery catheter 110 has a proximal end 810 and a distal end 815 that can be deployed to a target location in a patient's bronchial passageway, such as through the trachea. The catheter 110 has an elongated outer shaft 820 and an elongated inner shaft 825 that is slidably positioned within the outer shaft 820 such that the outer shaft 820 can slidably move relative to the inner shaft 825 along the length of the catheter, as described in more detail below.

The following references describe exemplary delivery devices: U.S. Pat. No. 5,954,766 entitled "Body Fluid Flow Control Device"; U.S. patent application Ser. No. 09/797,910, entitled "Methods and Devices for Use in Performing Pulmonary Procedures"; U.S. patent application Ser. No. 10/270,792, entitled "Bronchial Flow Control Devices and Methods of Use"; and U.S. patent application Ser. No. 10/448,154, entitled "Guidewire Delivery of Implantable Bronchial Isolation Devices in Accordance with Lung Treatment". The foregoing references are all incorporated by reference in their entirety and are all assigned to Emphasys Medical, Inc., the assignee of the instant application.

With reference still to FIG. 8, an actuation handle 830, is located at the proximal end 810 of the catheter 110; The actuation handle 830 can be actuated to slidably move the outer shaft 820 in a proximal direction relative to the inner shaft 825 with the inner shaft 825 remaining fixed relative to the actuation handle 830. During such movement, the outer shaft 820 slides over the inner shaft 825. FIG. 8 shows a schematic view of the actuation handle 830, which is described in more detail below. Generally, the handle 830 includes a first piece 835 and a second actuation piece 840, which is moveable relative to the first piece 835. The outer shaft 820 of the catheter 110 can be moved relative to the inner shaft 825 by moving the first piece 835 of the handle 830 relative to the second piece 840.

The inner shaft 825 of the catheter 110 can include a central guidewire lumen (not shown) that extends through the entire length of the catheter 110. The central guidewire lumen of the inner shaft 825 is sized to receive a guidewire, which can be used during deployment of the catheter 110 to guide the catheter 110 to a location in a bronchial passageway.

With reference still to FIG. 8, a housing 850 is located at or near a distal end of the catheter 110 for holding therein the bronchial isolation device 115. In one embodiment, the housing 850 is attached to a distal end of the outer shaft 820 of the catheter 110 but not attached to the inner shaft 825, which extends axially through the housing. The housing 850 defines an inner cavity that is sized to receive the bronchial isolation device 115 therein.

Figure 9:
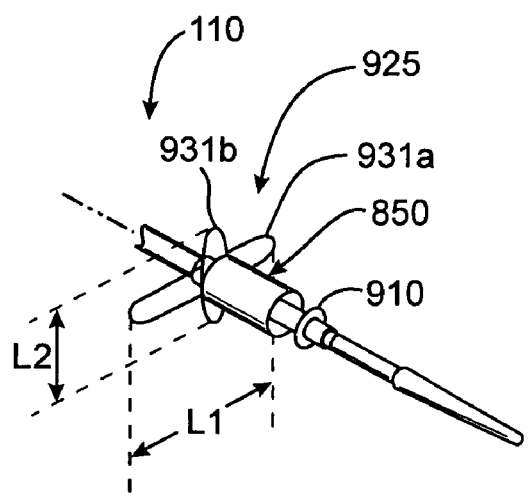
FIG. 9 shows a perspective view of a distal region of the delivery catheter.
Figure 10A:
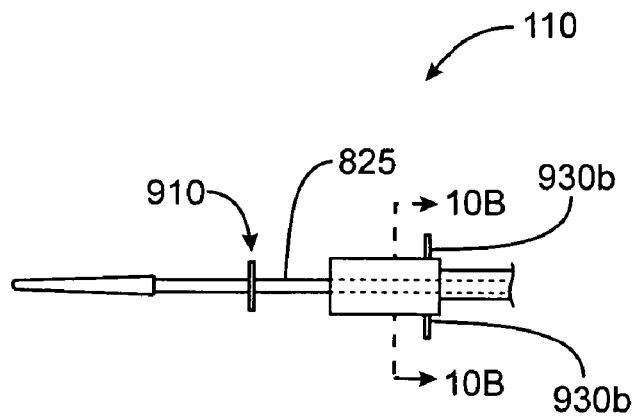
FIG. 10A shows a plan, side view of the distal region of the delivery catheter.

FIG. 9 shows an enlarged, perspective view of the distal portion of the catheter 110 where the housing 850 is located. FIG. 10A shows a plan, side view of the distal portion of the catheter 110 where the housing 850 is located. As shown in FIGS. 9 and 10A, the housing 850 is shaped to receive the bronchial isolation device therein and is open at a distal end and closed at a proximal end. The inner shaft 825 of the catheter 110 protrudes through the housing 850 and can slidably move relative to the housing 850. An ejection member, such as a flange 910, is attached at or near a distal end of the inner shaft 825. The flange 910 is sized such that it can be received into the housing 850 so that the flange 910 can be withdrawn into the housing 850 to abut a proximal end of the housing. FIGS. 9 and 10A show the flange 910 positioned outside of the housing 850.

As described below, the ejection member can be used to eject the bronchial isolation device 115 from the housing 850. The housing can be manufactured of a rigid material, such as steel. The housing 850 can also be flexible or collapsible. Although the housing 850 is shown having a cylindrical shape, it should be appreciated that the housing 850 can have other shapes that are configured to receive the bronchial isolation device therein.

Figure 10B:
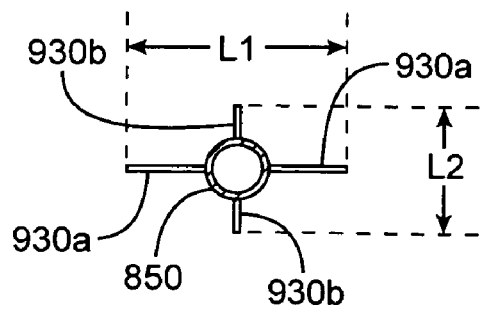
FIG. 10B shows a cross-sectional view of the delivery catheter along line 10B-10B of FIG. 10A.

In one embodiment, a sizing element 925 is located at or near the housing 850, as shown in FIGS. 10A and 10B. (For clarity of illustration, FIG. 10B does not show the bronchial isolation device 115 mounted in the housing 850 and does not show the inner shaft 825 of the delivery catheter.) The sizing element 925 can be used to determine whether the bronchial isolation device 115 in the housing 850 will fit within a particular bronchial passageway in a working manner. The sizing element 925 comprises one or more extensions, such as first extensions 930a and second extensions 930b that define distances L1 and L2, respectively. That is, the opposed, outer tips of the extensions 930a are separated by a distance L1 and the opposed, outer tips of the extensions 930b are separated by a distance L2. The distance L1 corresponds to the diameter of the larger end of the functional diameter range of the bronchial isolation device 115. That is, the distance L1 is substantially equal to the largest possible diameter for a bronchial passageway in which the bronchial isolation device can be functionally deployed. The distance L2 corresponds to the diameter of the lower end of the functional diameter range of the bronchial isolation device 115. That is, the distance L2 is substantially equal to the smallest possible diameter for a bronchial passageway in which the bronchial isolation device 115 can be functionally deployed. It should be appreciated that the extensions 930 can take on a variety of structures and shapes. For example, FIGS. 10A and 10B shows the extensions 930 comprising elongate prongs that extend radially outward from the catheter or the housing 850.

In another embodiment, shown in FIG. 9, the extensions 930 of the sizing element 925 comprise two or more loops 931a and 931b, which correspond to the extensions 930a and 930b, respectively. Each loop 931 forms an ellipse having a long axis of a predetermined length. In the illustrated embodiment, the loop 931a has a long axis of length L1 that is greater than the length L2 of the long axis of the second loop 931b. Thus, the larger length L1 of loop 931a corresponds to the diameter of the larger end of the functional diameter range of the bronchial isolation device 115. The shorter length L2 of loop 931b corresponds to the diameter of the lower end of the functional diameter range of the bronchial isolation device.

As the delivery catheter 110 is inserted into the bronchial passageway, the sizing element 925 is used to determine whether or not the bronchial passageway is within the functional range of the bronchial isolation device 115. For a bronchial passageway in which the sizing element is positioned, if the opposed tips of the longer extensions 930a (e.g., the diameter loop 931a) cannot simultaneously contact the wall of the bronchial passageway, then the bronchial isolation device 115 is too small to be implanted in that passageway. In other words, the bronchial passageway is too large for the bronchial isolation device if the tips of the longer extensions 930a cannot simultaneously contact the bronchial wall when the extensions 930a are centrally positioned within the bronchial passageway. If the opposed tips of the shorter extensions 930b can simultaneously contact the wall of the bronchial passageway, then the bronchial isolation device 115 is too large to be implanted in the bronchial passageway in a working manner.

The extensions 930, such as the loops 931, can be constructed of various materials. In one embodiment, the extensions are constructed of wire, etched from a flat plate, or by other methods. The extensions 930 can be made of a flexible material, such as Nitinol, or a polymer or other flexible material, such that the extensions fold down when inserted into or retracted into the working channel of the bronchoscope. In one embodiment, the extensions are manufactured of Pebax, which is a polyether-block co-polyamide polymer. Other flexible resins can be used as well. Other configurations and shapes of the sizing element 925 are contemplated, such as standing struts rather than loops, etc.

If the bronchial isolation device 115 is manufactured in more than one size, the sizing element 925 can be made in different sizes to correspond with each size of bronchial isolation device 115. The range of bronchial lumen diameters in which different sizes of bronchial isolation device can be implanted can be chosen such that the ranges overlap. For example, the smallest acceptable diameter for a larger size of bronchial isolation device can be smaller than the largest acceptable diameter for the next smaller size of bronchial isolation device. Each size can be delivered with a delivery catheter 110 that has a sizing element 925 with extensions 930 that correspond to the functional range of the particular size of bronchial isolation device.

When multiple sizes of bronchial isolation devices 115 are available, each can be delivered with a delivery catheter 110 that incorporates a sizing element 925 with extensions 930 of a size that correspond to the maximum and minimum acceptable bronchial lumen diameters for that device. This would require that the physician or other medical practitioner implanting the bronchial isolation devices estimate the size of the appropriate device for the target bronchial lumen prior to implanting the first device. The corresponding catheter package would then be opened, and the catheter inserted into the bronchoscope, and the sizing element 925 used to check the diameter of the target bronchial lumen.

If the operator has chosen the wrong size of device, the delivery catheter 110 would have to be removed from the bronchoscope and the next larger or smaller catheter chosen. This procedure might require the operator to use an extra delivery catheter and/or bronchial isolation device, and to spend extra time changing to the appropriately sized device.

Figure 23:
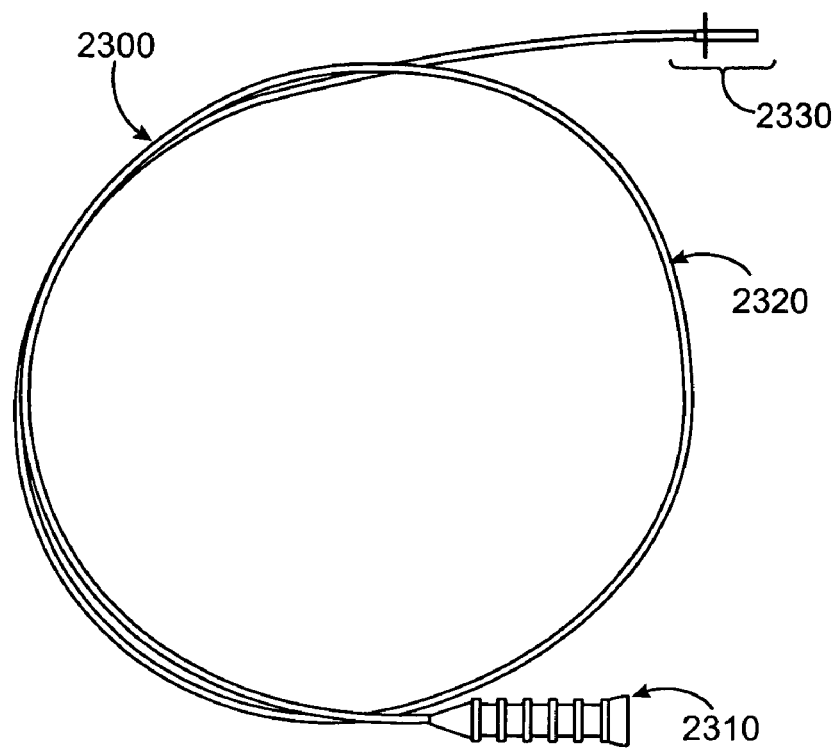
FIG. 23 shows a sizing catheter with a sizing element on a distal end of the catheter.

In an alternative embodiment, the sizing element 925 can be mounted on the distal end of a sizing catheter 2300, as shown in FIG. 23, rather than on the distal end of the delivery catheter 110. The sizing catheter comprises a flexible shaft 2320, a handle 2310 mounted to the proximal end of the flexible shaft 2320, and a sizing element 2330 mounted to the distal end of the flexible shaft. The sizing catheter 2300 is inserted through a suitable delivery device (such as through the working channel of the bronchoscope or other endoscope), placed into the target bronchial lumen, and used to size the target bronchial lumen prior to the insertion of the delivery catheter 110 with the bronchial isolation device 115 loaded into the distal end of the catheter. In this way, the appropriate size of bronchial isolation device 115 would be chosen prior to opening any delivery catheter or bronchial isolation device packages.

Figure 24:
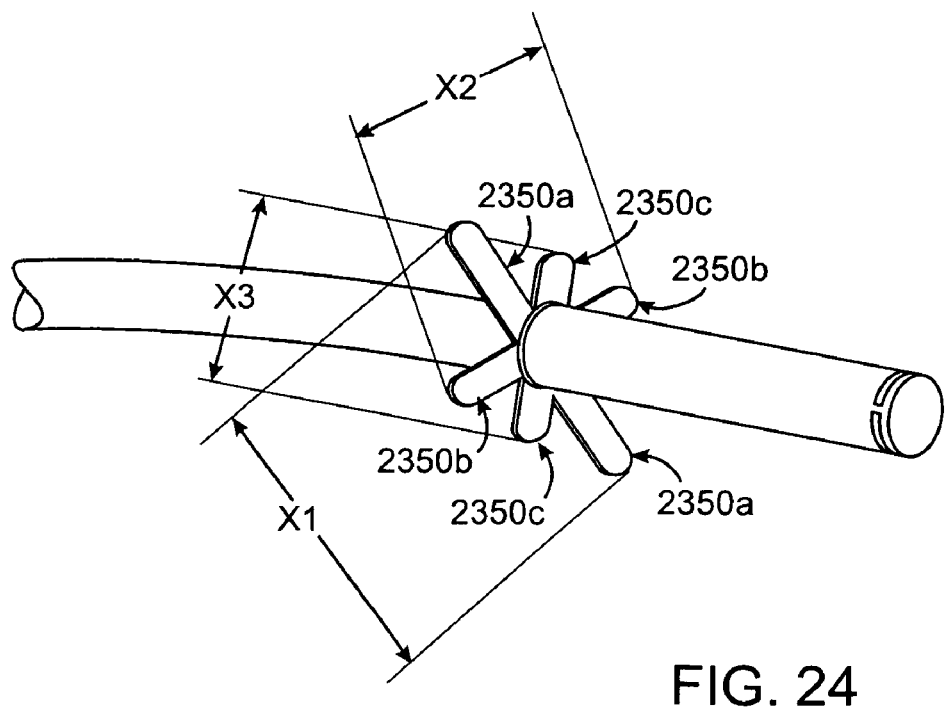
FIG. 24 shows an enlarged view of one embodiment of the sizing element.

The sizing catheter 2300 can be designed to size bronchial lumens for just one size of bronchial isolation device 115. In this situation, as with the sizing element 925, the sizing element 2330 is mounted to the distal end of the sizing catheter 2300, and is comprised of two sets of sizing extensions 930a and 930b, one corresponding to the minimum operational diameter and one corresponding to the maximum operational diameter of the bronchial isolation device 115. Alternately, if there are two sizes of bronchial isolation device 115, the sizing element 2330 can be comprised of three sets of sizing extensions 2350 as shown in FIG. 24. The length X1 of the longest set of extensions 2350a correspond to the maximum diameter of the larger of the two sizes of bronchial isolation devices 115. The length X3 of the shortest set of extensions 2350c correspond to the minimum diameter of the smaller of the two sizes of bronchial isolation devices 115. The length X2 of the intermediate set of extensions 2350b corresponds to the transition diameter between the two bronchial isolation devices 115. If the lumen is larger in diameter than X2, then the larger of the two bronchial isolation devices is implanted, and if the lumen is smaller in diameter than X2, than the smaller of the two bronchial isolation devices is implanted.

If there are three different sizes of bronchial isolation devices, then the sizing catheter 2300 can be manufactured with four sets of sizing extensions. The smaller of the two intermediate sets of extensions correspond to the transition diameter between the smallest and the intermediate size bronchial isolation device, and the larger of the two intermediate sets of extensions correspond to the transition diameter between the intermediate and the largest size bronchial isolation device. Of course, the number of sizing extensions 2350 could be increased appropriately as the number of bronchial isolation device sizes increases, however at some point it would become impractical to add additional sizing extensions to the catheter.

More than one size of sizing catheter can be manufactured to solve this problem with each one covering the size range of a different set of bronchial isolation devices. For example, one sizing catheter can be designed to size a small and a medium size of bronchial isolation device, and another sizing catheter designed to size the medium size and a large size of bronchial isolation devices. If there are four sizes of device, one sizing catheter can be designed to size the first and second size of bronchial isolation device, and a second sizing catheter can be designed to size the third and fourth size of bronchial isolation devices.

Figure 25:
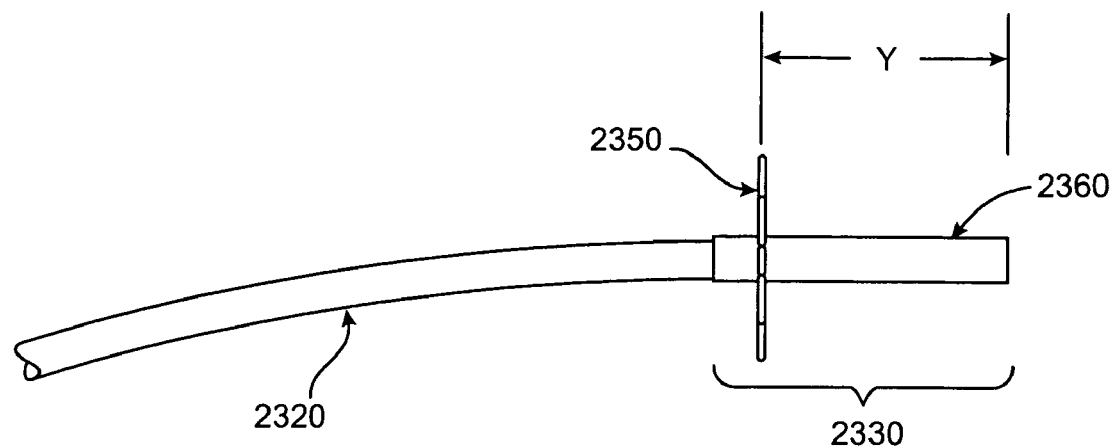
FIG. 25 shows a side view of a sizing element having a depth measuring extension.

An additional feature of the sizing element 2330 is shown in FIG. 25. A bronchial lumen depth measuring extension 2360 comprising an elongate post extends beyond the sizing elements 2350 along the axis of the shaft 2320. The length of the depth measuring element 2360 is "Y" and this corresponds to the length of the portion of the bronchial isolation device 115 that contacts the bronchial lumen wall when the bronchial isolation device is positioned in the bronchial passageway. By placing the distal tip of the depth measuring element 2360 against the distal end of the target bronchial lumen (this is often the tip of the carina of the next more distal bifurcation), the operator can visualize the location of the sizing elements 2350. If the sizing elements are proximal of the proximal end of the target bronchial lumen, than the device is too long for the target bronchial lumen. If the sizing elements are distal to the proximal end of the target bronchial lumen, than the device will not be too long for the bronchial lumen.

As mentioned previously, the sizing element 2330 can be constructed of a flexible material that would allow the sizing extensions 2350 to fold back against the shaft 2320 in order to allow the sizing catheter 2300 to be inserted through the working channel of a bronchoscope or other endoscope for sizing, and then removed. The extensions can be formed of a flexible metal such as stainless steel or nitinol, or of a polymer such as thermo plastic elastomer.

The handle 2310 can be made of any appropriate material such as metal or plastic, and is preferably made with texture or ribs on the surface to allow it to be easily gripped with a gloved hand. The flexible shaft 2320 is desirably flexible enough to allow it to pass through the working channel of an articulated bronchoscope or other endoscope. The shaft 2320 is also desirably stiff enough under compressive and tensile loads so that it may be pushed through the endoscope working channel and later pulled to remove it. It is also desirably stiff enough in torsion so that the sizing element 2330 rotates in concert with rotation of the handle 2310 without undo "windup" of the shaft.

To achieve the aforementioned features, there are a number of different possible construction techniques for the flexible shaft. The shaft can be constructed from a solid flexible material such nylon or other polymer, or metal such as nitinol or stainless steel. It may be formed by coiling or braiding metal wire such as stainless steel or nitinol to form a shaft. It may be formed of a composition of two or more materials such as a braided wire shaft fused with a polymer tube. One composition that works particularly well is a solid PTFE (PolyTetraFluoroEthylene) core covered with a co-extrusion of nylon. Stainless steel wire is then braided on top of this core and a tubular polyether block amide (Pebax) extrusion is then fused over the wire so that the Pebax melts through the stainless steel wire and fuses to the nylon layer. This results in a very flexible shaft that transmits torque well to the sizing element 2330, and is stiff along the shaft length to allow the catheter to pushed through the endoscope working channel without kinking.

Figure 26:
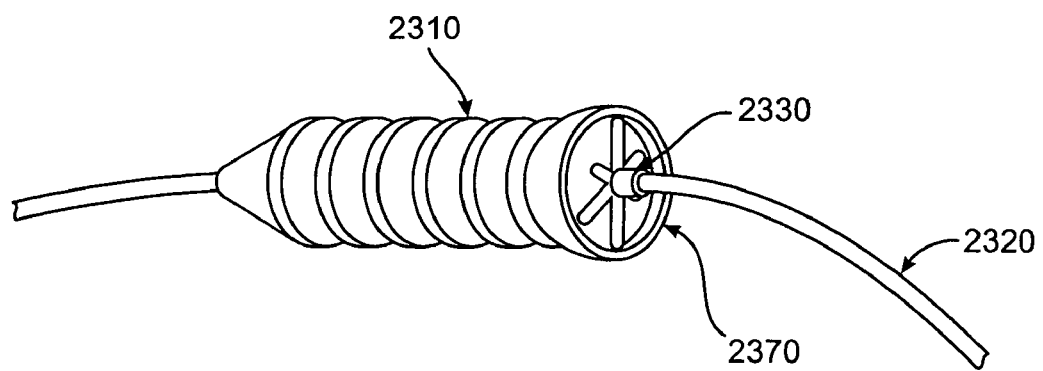
FIG. 26 shows a perspective view of a handle of the sizing catheter, the handle including a cavity that receives at least a portion of the sizing element.

An optional feature of the sizing catheter 2300 is shown in FIG. 26. The distal end of the handle 2310 has a hole, indentation or cavity that is sized to fit or receive the depth measuring element 2360. In order to package the sizing catheter 2300, the catheter can be coiled and the depth measuring element 2360 inserted into the hole in the handle 2310 to both keep the catheter coiled and to protect the sizing element 2330 from damage. The handle 2310 may also have a raised rim 2370 that acts to protect the sizing extensions 2350 from damage.

Figure 11A:
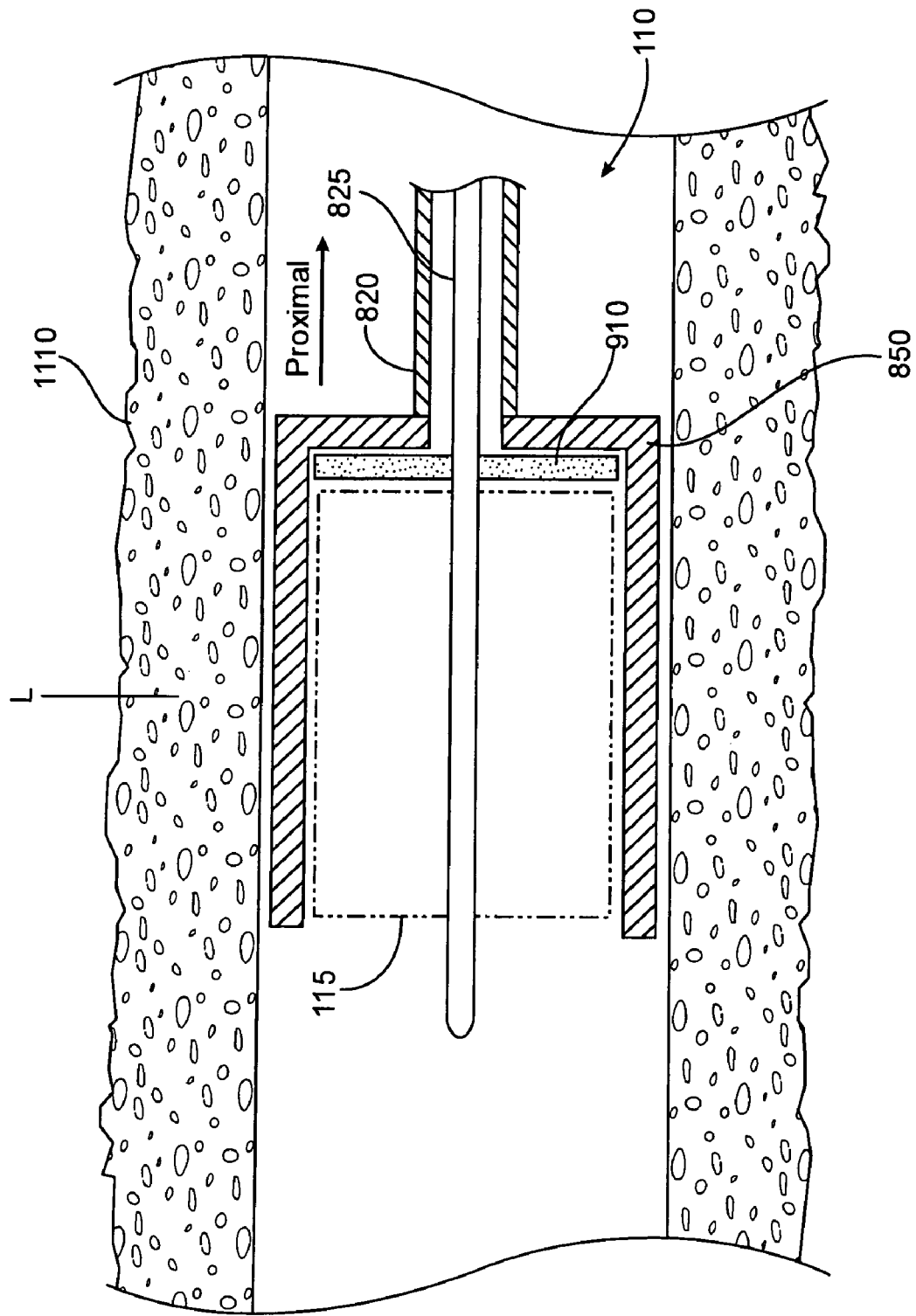
FIG. 11A shows the delivery catheter containing a bronchial isolation device in a housing, which is positioned at a location L of a bronchial passageway.

In use, the bronchial isolation device 115 is first inserted into the housing 850. The bronchial isolation device 115 can be inserted into the housing according to various methods and devices, some of which are described in U.S. patent application Ser. No. 10/270,792, entitled "Bronchial Flow Control Devices and Methods of Use", which is assigned to Emphasys Medical, Inc., the assignee of the instant application. After the bronchial isolation device 115 is inserted into the housing, the distal end of the delivery catheter 110 is deployed into a bronchial passageway via the trachea such that the housing 850 is located at or near the target location in the bronchial passageway, as shown in FIG. 11A. Once the delivery catheter 110 and the attached bronchial isolation device 115 are located at the target location, an operator can eject the bronchial isolation device 115 from the housing 850 into the bronchial passageway.

Figure 11B:
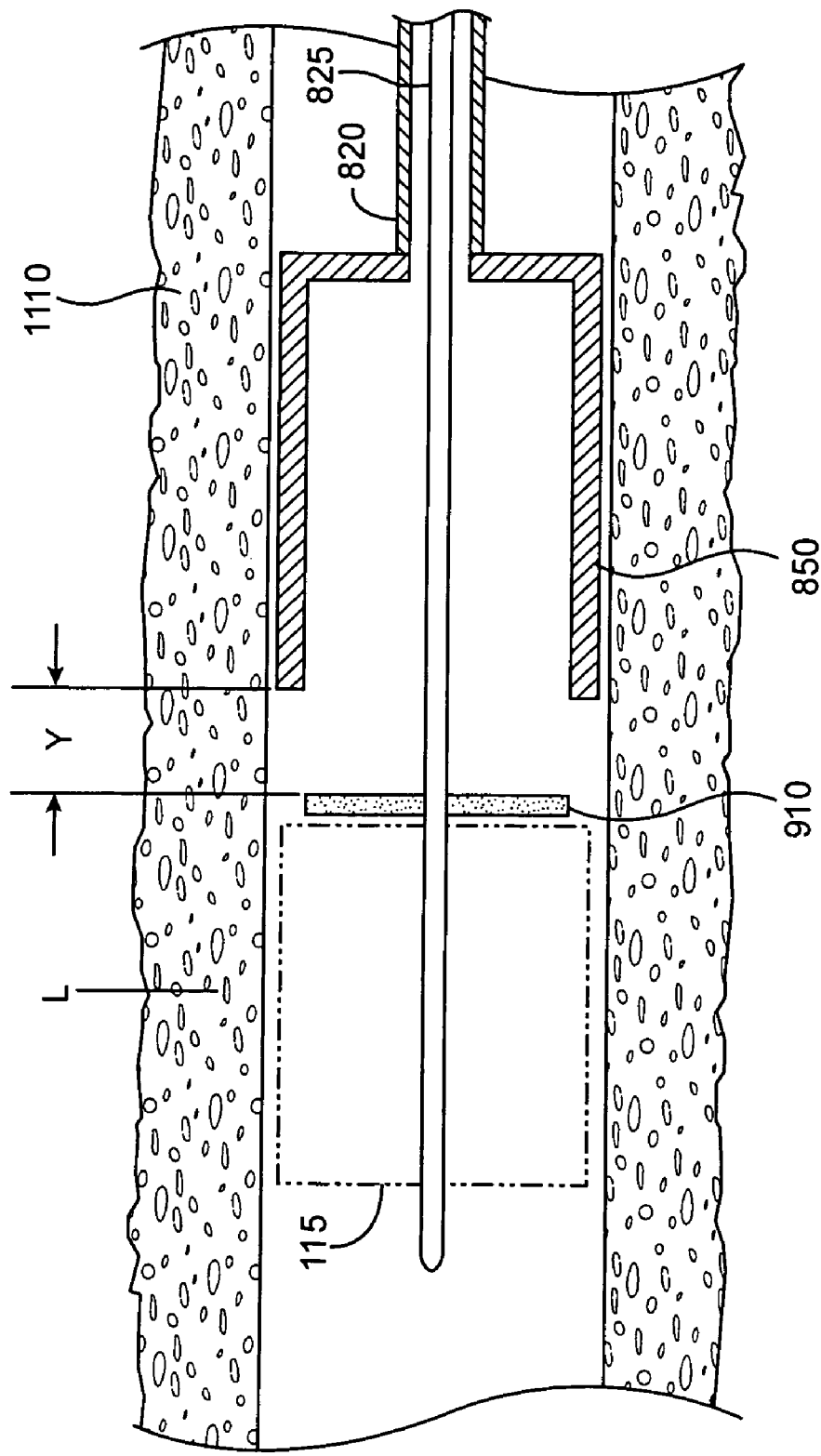
FIG. 11B shows the delivery catheter and the deployed bronchial isolation device at the location L of the bronchial passageway.

This process is described with reference to FIGS. 11A and 11B. FIG. 11A shows a cross-sectional view of a bronchial passageway 1110 with the deliver catheter 110 positioned therein. The distal end of the delivery catheter 110, including the housing 850, is located at or near the target location L. Once the catheter is positioned as such, an operator actuates the catheter handle 830 to slidably move the outer catheter member 820 in a proximal direction relative to the location L, while maintaining the location of the bronchial isolation device 115, inner shaft 825, and flange 910 fixed with respect to the location L. The proximal movement of the outer shaft 820 causes the attached housing 850 to also move in a proximal direction, while the flange 910 prevents the bronchial isolation device 115 from moving in the proximal direction. This results in the housing 850 sliding away from engagement with the bronchial isolation device 115 so that the bronchial isolation device 115 is eventually entirely released from the housing 850 and implanted in the bronchial passageway at the target location L, as shown in FIG. 11B.

Figure 12:
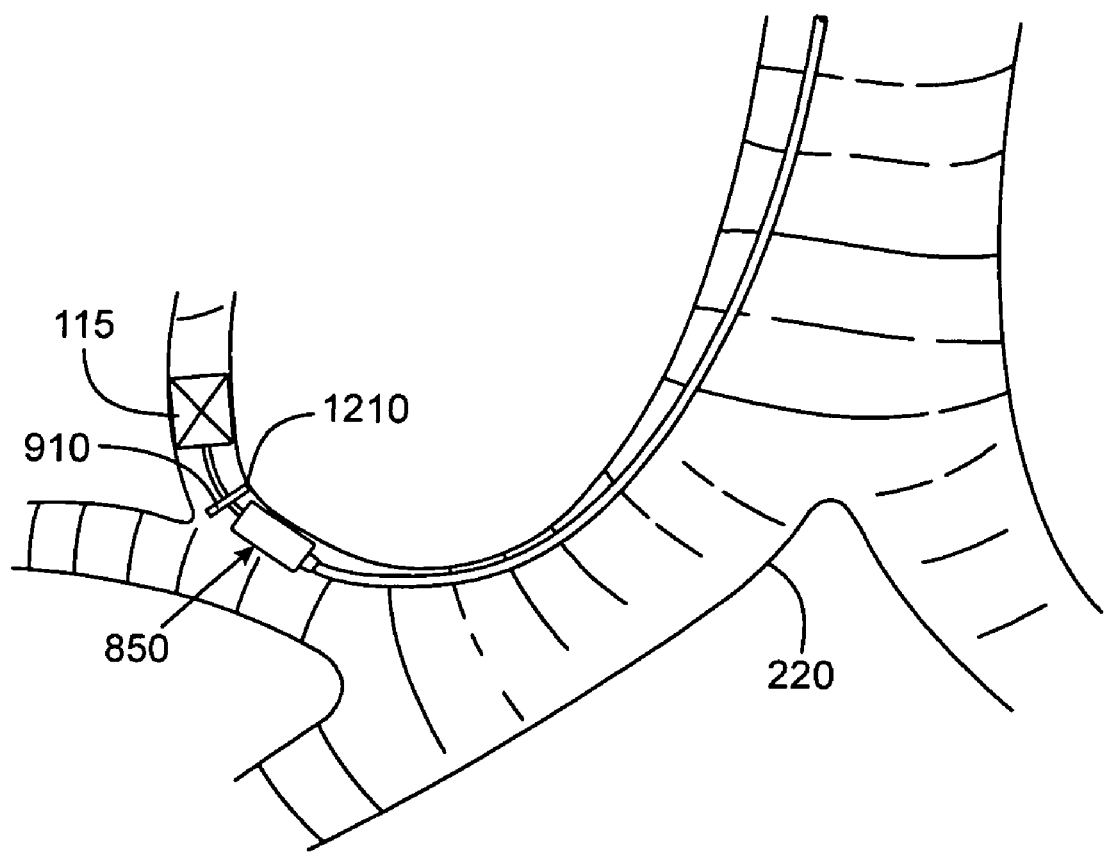
FIG. 12 shows a cross-sectional view of a delivery catheter deployed in a bronchial location that requires the delivery catheter's distal end to bend at an acute angle.

During actuation of the actuation handle 830, the outer shaft 820 can undergo tension and the inner shaft 825 undergo compression due to the relative movement of the shafts and possible friction against the proximal movement of the outer shaft 820. This can result in an axial shortening of the inner shaft 825 and an axial lengthening of the outer shaft 820. In order to compensate for this and to allow the device 115 to be fully ejected from the housing 850, the flange 910 can be configured to over-travel a distance Y beyond the distal end of the housing 850, as shown in FIG. 11B. The over-travel of the flange 910 beyond the housing's distal end can create a potential problem during withdrawal of the delivery catheter 110, particularly in situations where the delivery catheter 110 is deployed in a location that requires its distal end to bend at an acute angle. FIG. 12 shows such a situation, where the bronchial isolation device 115 is deployed at a location in the bronchial tree 220 that requires the delivery catheter 110 to bend at an acute angle with the flange 910 withdrawn entirely from the housing 850. In such situations, the flange 910 can catch on the tissue of the bronchial wall at a location 1210 inside the bend as the operator pulls the catheter 110 out of the bronchial passageway. This can make it difficult for an operator to remove the delivery catheter 110 from the bronchial passageway and can risk possible damage to the tissue if the operator continues to pull while the flange is caught on the bend.

Figure 13:
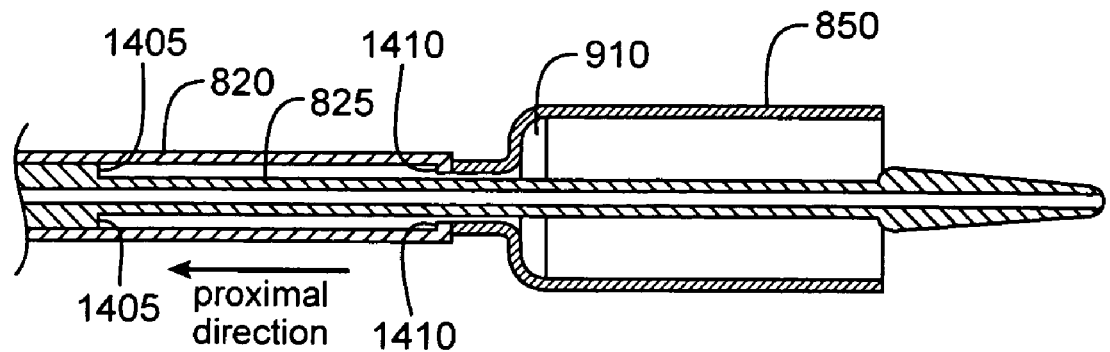
FIG. 13 shows a cross-sectional view of the distal end of the delivery catheter with a limited-travel flange fully retracted into the delivery housing.
Figure 14:
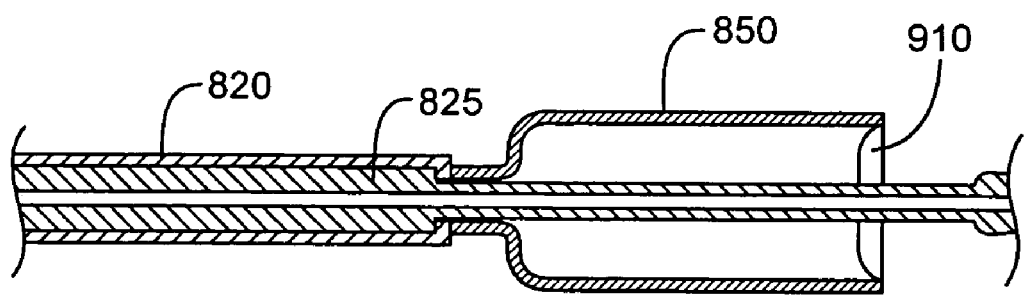
FIG. 14 shows a cross-sectional view of the distal end of the delivery catheter with a limited-travel flange fully extended.

This problem can be overcome by limiting the travel of the flange 910 relative to the housing 850 such that the flange 910 cannot move outward of the distal end of the housing 850. One way this can be accomplished is by limiting the travel of the inner shaft 825 at the distal end of the catheter 110. FIG. 13 shows a cross-sectional view of the distal region of the catheter, showing the inner shaft 825 axially disposed in the outer shaft 820. As mentioned, the flange 910 is attached to the inner shaft 825 and the housing 850 is attached to the outer shaft 820. The inner shaft 825 has a step 1405 and the housing 850 or outer shaft 820 has a stop or ledge 1410. The step 1405 is spaced from the ledge 1410 when the flange 910 is fully withdrawn in the housing 850. As the outer shaft 820 moves in the proximal direction, the step 1405 eventually abuts the ledge 1410, which acts as a stop to limit any further proximal movement of the outer shaft 820 relative to the inner shaft 825. As shown in FIG. 14, the flange 910 is positioned just at the distal end of the housing 850 when the stop position is reached. Thus, the flange 910 and housing 850 have a relative range of travel therebetween.

In one embodiment, the flange 910 is limited from being distally positioned at all past a distal edge of the housing. In another embodiment, the flange 910 can be distally positioned past the distal end of the housing only to the extent that the flange will not catch onto tissue during withdrawal of the delivery catheter. Thus, referring to FIG. 11B, the distance Y is sufficiently small to prevent or greatly reduce the likelihood of bronchial wall tissue being caught or pinched between the flange 910 and the housing 850 during withdrawal of the delivery catheter 110. This eliminates the possibility of the flange 910 catching or lodging on the bronchial tissue during removal of the delivery catheter 110.

Actuation Handle

Figure 15:
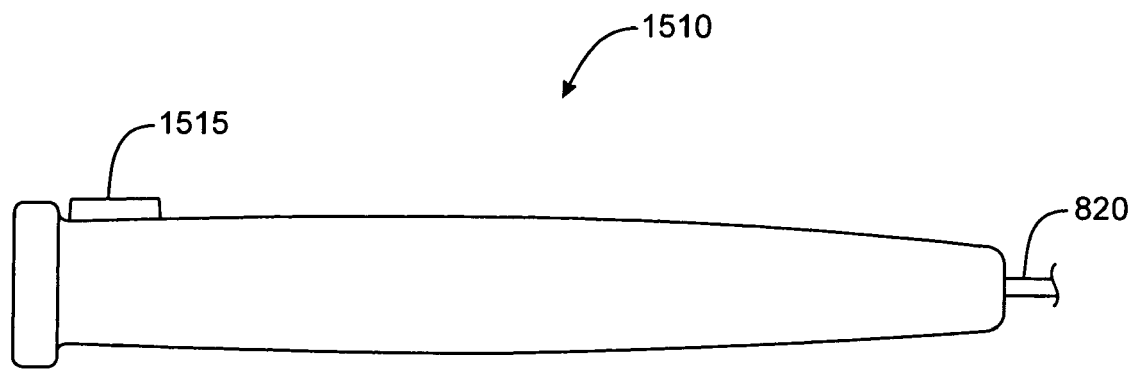
FIG. 15 shows a side view of one embodiment of an actuation handle of the delivery catheter.

There is now described an actuation handle for the delivery catheter that can be used to slide the outer shaft 820 (and the attached housing 850) relative to the inner shaft 825 while maintaining the inner shaft 825 stationary relative to the handle. FIG. 15 shows a side view of an actuation handle 1510. In the illustrated embodiment, the actuation handle 1510 has an elongate shape suitable for grasping within an operator's hand. It should be appreciated, however, that the shape of the actuation handle 1510 can vary. The actuation handle 1510 includes an actuation member, such as a slidable actuation slider 1515, that can be actuated to slide the outer shaft 820 relative to the inner shaft 825 (the inner shaft is not shown in FIG. 15) during ejection of the bronchial isolation device 115. The actuation member can be positioned on the handle 1510 such that an operator can grasp the handle with a single hand and also move the actuation member using a finger or thumb of the same hand. For example, in the embodiment shown in FIG. 15, the slider 1515 is positioned along the side of the actuation handle 1510 so that the operator's thumb can be used to move the slider 1515. Other configurations can be used.

Figure 16:
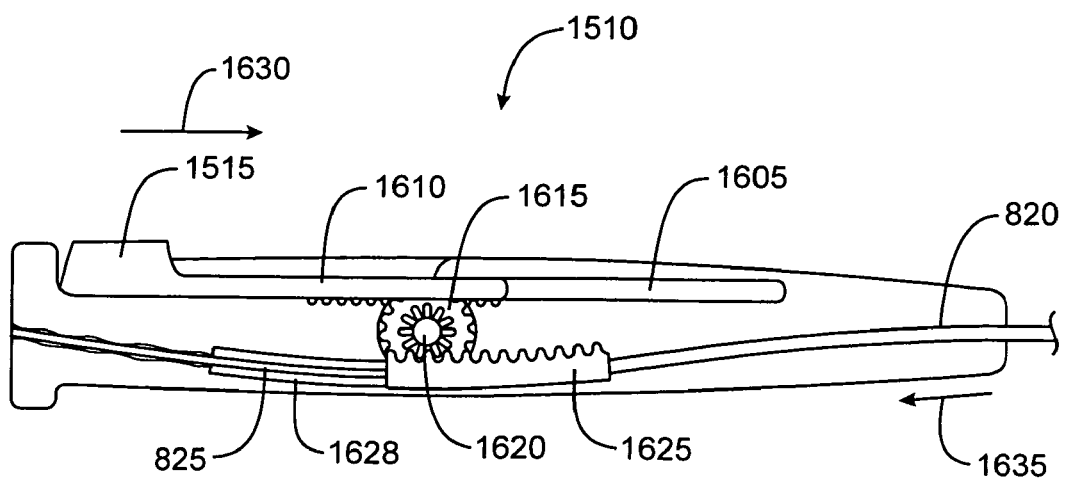
FIG. 16 shows a cross-sectional, side view of the actuation handle of FIG. 15 with an actuation member in an initial position.

FIG. 16 shows a cross-sectional view of the actuation handle 1510, which includes an actuation system for moving the outer shaft relative to the handle. In one embodiment, the actuation system comprises a rack and pinion system for effecting movement of the outer shaft 820 relative to the inner shaft 825. The actuation slider 1515 is coupled to the actuation system. The actuation slider 1515 is slidably positioned inside an elongate slot 1605 in the actuation handle 1510. A distal end of the actuation slider 1515 abuts or is attached to a first rack 1610 that is also slidably mounted in the elongate slot 1605. The first rack 1610 has a first edge with teeth that mesh with corresponding teeth on a first pinion 1615. The first pinion 1615 is engaged with a second pinion 1620 having teeth that mesh with a second rack 1625 mounted in an elongate slot 1628. The second rack 1625 is attached to the outer shaft 820 of the delivery catheter 110 such that movement of the second rack 1625 corresponds to movement of the outer shaft 820. That is, when the second rack slidably moves in the proximal direction or distal direction, the outer shaft 820 also moves in the proximal or distal direction, respectively. The inner shaft 825 is fixedly attached to the handle 1510, such as by using adhesive or through a friction fit. The first rack, second rack, first pinion, and second pinion collectively form a rack and pinion system that can be used to transfer distal movement of the actuation slider 1515 to proximal movement of the outer shaft 820 while the inner shaft 825 remains stationary relative to the handle 1510, as described below.

The actuation slider 1515 can be positioned in an initial position, as shown in FIG. 16. When the actuation slider 1515 is in the initial position, the flange 910 is fully withdrawn inside the housing 950 (as shown in FIG. 13). In one embodiment, the actuation slider 1515 is at the proximal end of the handle when in the initial position, although it should be appreciated that the initial position can vary. When the actuation slider 1515 slidably moves in the distal direction (represented by the arrow 1630 in FIG. 16) from the initial position, the rack and pinion system causes the outer shaft 820 to slidably move in the proximal direction (represented by the arrow 1635 in FIG. 16), and vice-versa, while the inner shaft 825 remains stationary relative to the handle. More specifically, movement of the actuation slider 1515 in the distal direction 1630 moves the rack 1610 in the distal direction, which drives the first pinion 1615 and which, in turn, drives the second pinion 1620. The gearing between the second pinion 1620 and the second rack 1625 causes the second rack 1625 to move in the proximal direction 1635 through the slot 1628. As mentioned, the second rack 1625 is attached to the outer shaft 820 so that the outer shaft 820 moves in the proximal direction 1635 along with the second rack 1625. During such movement, a distal region of the outer shaft 820 slides into the handle 1510. While this occurs, the inner catheter 825 (which is fixed to the handle 1510) remains stationary relative to the handle 1510 while the outer shaft 820 moves. Thus, when the operator moves the slider 1515 in the distal direction 1630, the outer shaft 820 (and the attached housing 850) slides in the proximal direction, with the inner shaft 820 and flange 910 remaining stationary relative to the handle. The handle can be fixed relative to the patient such that the handle, inner shaft, flange and bronchial isolation device remain fixed relative to the patient during ejection of the bronchial isolation device from the housing.

The gear ratio between the first pinion 1615 and second pinion 1620 can be varied to result in a desired ratio of movement between the actuation slider 1515 and the outer catheter 820. For example, the first pinion 1615 can have a larger diameter than the second pinion 1620 so that the outer shaft 820 (and the attached housing 850) are withdrawn in the proximal direction at a slower rate than the actuation slider 1515 is advanced in the distal direction. The gear ratio can also be varied to reduce the force required to move the actuation slider 1515 and thereby make it easier for an operator to control ejection of the bronchial isolation device 115 from the housing 850. The ratio between the pinions can be altered to make the withdrawal of the outer shaft faster, slower, or the same speed as the actuation slider movement. In one embodiment, the rack and pinion system is configured such that a 2:1 force reduction occurs such that the actuator slider moves about twice the distance that the outer shaft 820 is moved. For example, if the slider is moved an inch in the distal direction, then the outer shaft and the attached housing moves about half an inch in the proximal direction, and vice-versa.

The handle 1510 can include a safety lock that retains the actuation slider 1515 (or any other type of actuation member) in the initial position until the operator applies a force to the actuation slider sufficient to disengage the safety lock. The safety lock prevents inadvertent deployment of the bronchial isolation device either by inadvertent movement of the actuation slider in the distal direction or by inadvertent movement of the outer shaft 820 in the proximal direction relative to the handle. Inadvertent proximal movement of the outer shaft 820 can possibly occur when the delivery catheter 110 is being advanced into the patient's trachea, which can cause resistance to be applied to the outer shaft 820 by an anesthesia adaptor valve, endotracheal tube, or the lung.

Figure 17:
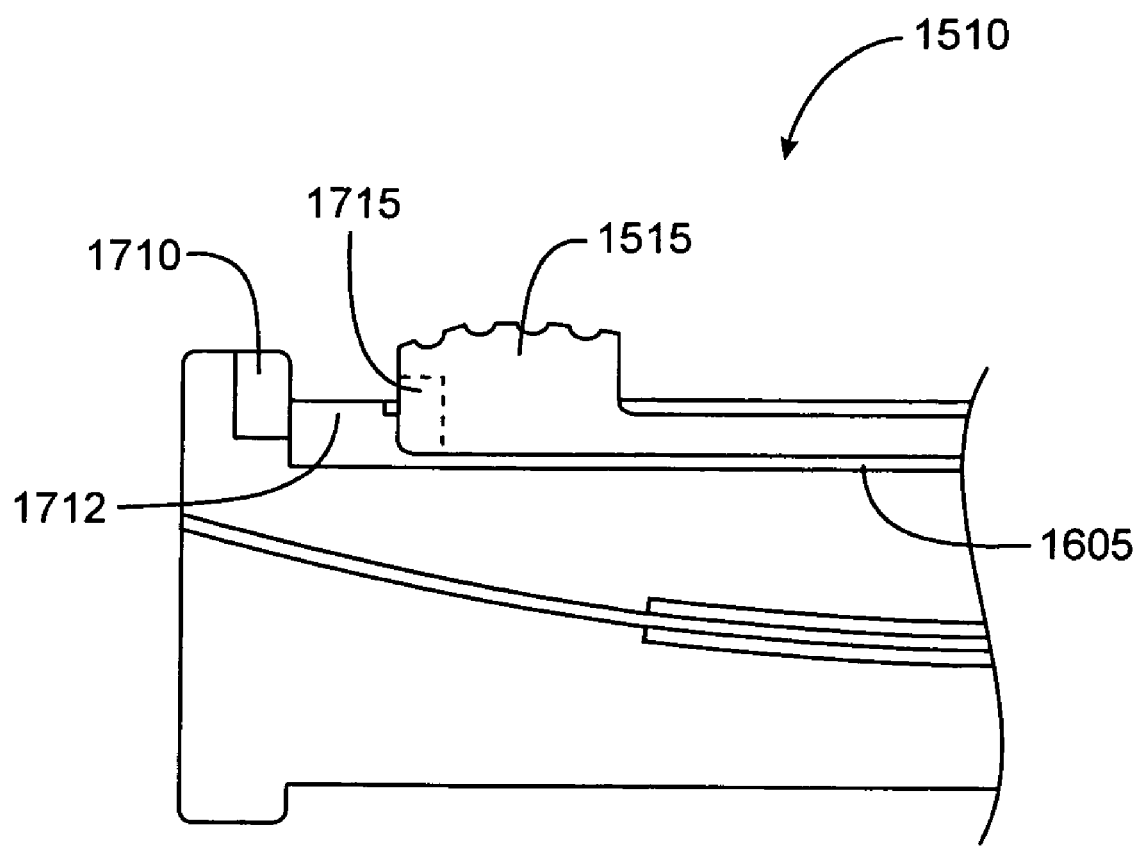
FIG. 17 shows a cross-sectional, side view of a portion of the actuation handle of FIG. 15 with the actuation member distal of the initial position.

In one embodiment, the safety lock comprises one or more magnets positioned in the actuation handle 1510. FIG. 17 shows a partial, cross-sectional view of the proximal end of the handle 1510 with the actuation slider 1515 positioned distally of the initial position. A first magnet 1710 is located on the handle 1510 near the initial location of the actuation slider 1515. A second magnet 1715 is located on or in the actuation slider 1515. The magnets 1710, 1715 are oriented such that an attractive magnetic force exists therebetween. When the actuation slider 1515 is in the initial position, the magnetic force between the magnets 1710, 1715 retains the actuation slider 1515 in the initial position until the operator applies a force to the slider 1515 sufficient to overcome the magnetic force and move the slider 1515 out of the initial position.

It should be appreciated that configurations other than magnets can be employed as the safety lock. One advantage of magnets is that the attractive force between the magnets 1710, 1715 automatically increases as the actuation slider moves toward the initial position. If the actuation slider happens to be out of the initial position when the bronchial isolation device is loaded into the housing 850, the actuation slider 1515 is driven back toward the initial position as the bronchial isolation device is loaded into the housing 850. The magnetic attraction between the first and second magnets 1710, 1715 automatically engages the safety lock when the actuation slider 1515 moves into the initial position.

The safety lock can include an additional feature wherein the operator must depress the actuation slider 1515 in order to disengage the slider from the initial position. As shown in FIG. 17, the slot 1605 in the actuation handle 1510 has an opening 1712. The actuation slider 1515 moves outward and sits in the opening 1712 when in the initial position. The operator must depress the slider 1515 to move the actuation slider 1515 out of the opening in order to disengage the slider from the initial position and slide the actuation slider 1515 in the distal direction.

Adjustment of Handle Position Relative to Bronchoscope

As discussed above, according to the transcopic delivery method, the bronchoscope 120 (shown in FIGS. 1, 6, 7) is used in deploying the delivery catheter 110 into the bronchial passageway. Pursuant to this method, the delivery catheter 110 is inserted into the working channel 710 of the bronchoscope 120 such that the delivery catheter's distal end is aligned with or protrudes from the distal end of the bronchoscope 120. The bronchoscope 120, with the delivery catheter 110 positioned as such, is then inserted into the bronchial passageway via the patient's trachea such that the distal end of the delivery catheter is positioned at a desired location in the bronchial passageway, as shown in FIG. 1. It should be appreciated that the delivery catheter 110 can be inserted into the bronchoscope 120 either before or after the bronchoscope has been inserted into the bronchial passageway.

Figure 18:
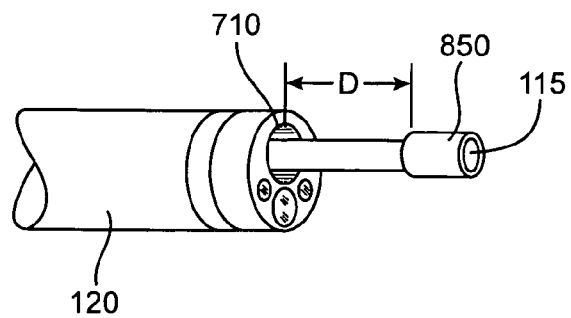
FIG. 18 shows an enlarged view of the distal region of the bronchoscope with the delivery catheter's distal end protruding outward from the working channel.

FIG. 18 shows an enlarged view of the distal region of the bronchoscope 120 with the delivery catheter's distal end (including the housing 850) protruding outward from the working channel 710. The bronchial isolation device 115 is positioned within the housing 850. The bronchial isolation device 115 is a distance D from the distal end of the bronchoscope 120. Once the bronchoscope and delivery catheter are in the patient, the operator may desire to adjust the distance D to fine tune the location of the bronchial isolation device 115. However, it can also be desirable or even required to hold the actuation handle 1510, and thus the inner shaft 825, stationary relative to the bronchoscope 120. This way, the bronchoscope 120 can be fixed relative to the patient's body, thereby keeping the bronchial isolation device 115 fixed relative to the target location in the bronchial passageway.

Figure 19:
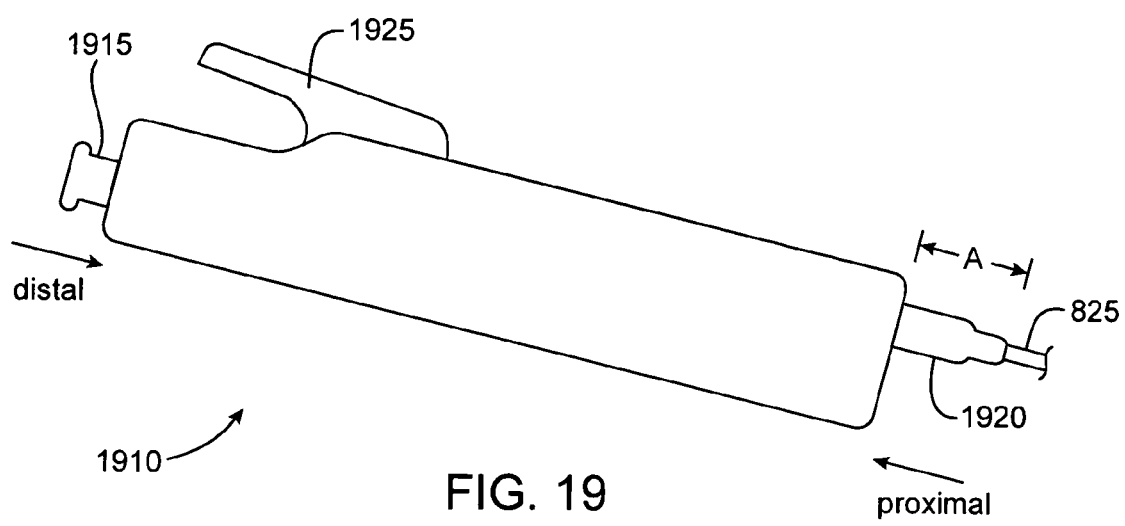
FIG. 19 shows another embodiment of the delivery catheter handle configured for transcopic delivery.

FIG. 19 shows another embodiment of the actuation handle, referred to as actuation handle 1910, that can be used for transcopic delivery and that can be fixed relative to a bronchoscope while also allowing for adjustments in the distance D of FIG. 18 once the delivery device is positioned in the bronchoscope. The actuation handle 1910 includes an actuation member in the form of a button 1915 that can be depressed in the distal direction to move the outer shaft 820 of the delivery catheter in the proximal direction. The handle includes an adjustment mechanism that is used to adjust the position of the handle relative to the bronchoscope. The adjustment mechanism comprises an elongated bronchoscope mount 1920 that extends outwardly from the distal end of the actuation handle 1910 and extends at least partially over the catheter outer shaft 820 such that the outer shaft can slide freely within the bronchoscope mount 1920. The bronchoscope mount 1920 extends outward from the handle a distance A. The bronchoscope mount 1920 is slidably moveable into or out of the handle 1910 such that it can be pushed into or pulled out of the handle 1910 along the axis of the mount 1920 in order to adjust the distance A. In one embodiment the bronchoscope mount 1920 is biased outward, for example with a spring, so that its tendency is to be fully extended outward from the handle 1910. A locking mechanism includes a lock, such as a lever 1925, that can be depressed to lock the bronchoscope mount 1920 relative to the handle 1910 when the distance A is adjusted to a desired amount, as described below. Once the distance A is at a desired amount, the operator can lock the bronchoscope mount 1920 relative to the handle to fix the bronchoscope mount 1920 relative to the handle 1910.

Figure 20:
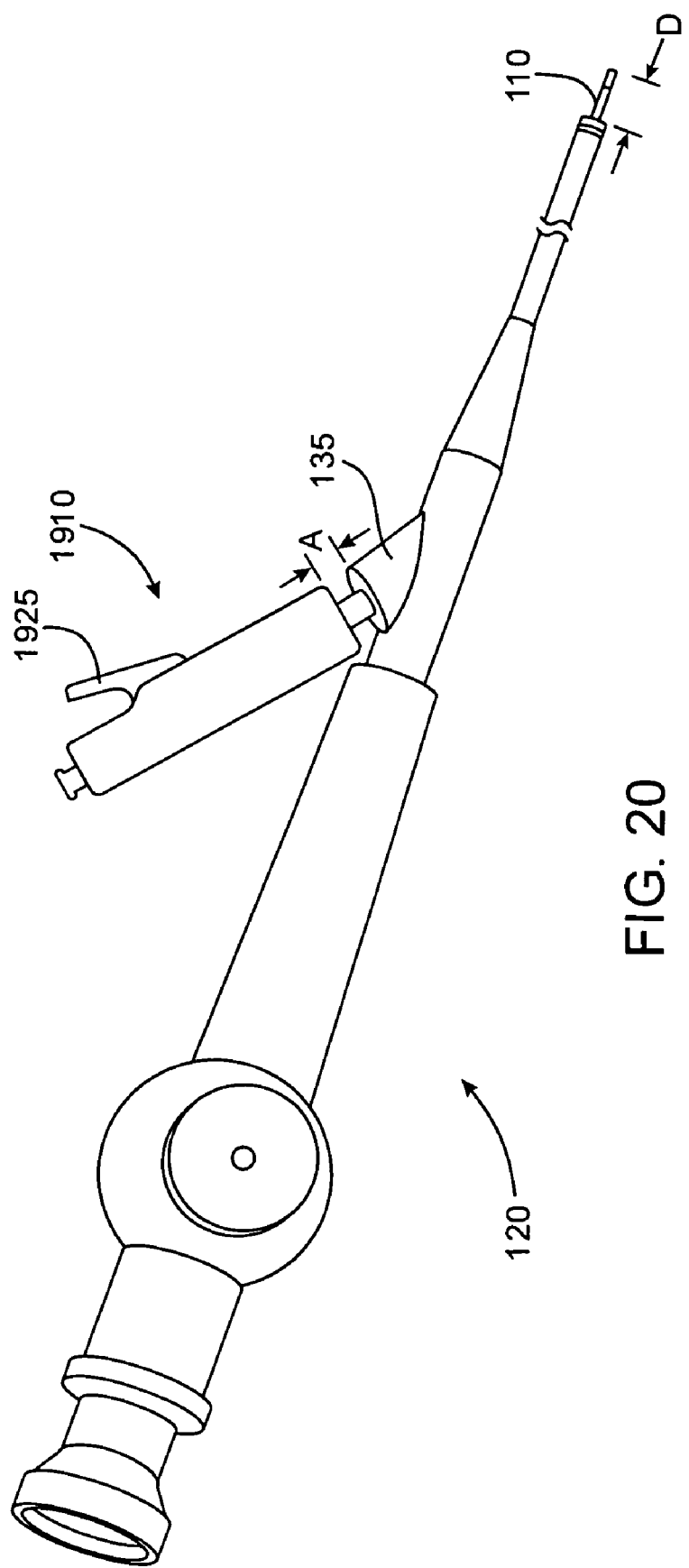
FIG. 20 shows the delivery catheter of FIG. 19 positioned within the working channel of the bronchoscope with the catheter handle protruding from the bronchoscope.

With reference to FIG. 20, the bronchoscope mount 1920 has a size and shape that is configured to sit within the entry port 135 of the bronchoscope working channel. In use, an operator can insert the bronchoscope mount 1920 into the entry port 135 such that it abuts and sits within the entry port 135. In this manner, the actuation handle 1910 is fixed relative to the bronchoscope 120 with the catheter's distal end protruding a distance D from the bronchoscope's distal end (as shown in FIG. 20). The operator can then adjust the distance A by moving the bronchoscope mount 1920 into or out of the handle 1910, such as by pushing on the handle 1910 to decrease the distance A. By virtue of the outer and inner catheter shafts' attachment to the handle, adjustments in the distance A will correspond to adjustments in D. That is, as the operator decreases the distance A (FIG. 20), the catheter slides deeper into the bronchoscope so that the distance D (FIG. 18) increases, and vice-versa.

Once the desired distance A has been achieved, the bronchoscope mount 1920 is locked by depressing the lever 1925. Thus, by adjusting the distance A, the operator also adjusts the distance D (shown in FIG. 18) between the distal end of the bronchoscope 120 and the bronchial isolation device 115. This can be helpful where different brands or types of bronchoscopes have different length working channels. It also allows the operator to fine-tune the position of the housing 850 and bronchial isolation device in the bronchial passageway without moving the bronchoscope. Other mechanisms for locking the movement of the bronchoscope mount 1920 are possible such as depressing and holding the lever 1925 to release the movement of the bronchoscope mount 1920, repositioning the bronchoscope mount 1920, and releasing the lever 1925 to lock the bronchoscope mount 1920 in place.

Catheter Sheath

As discussed above, during use of the delivery catheter 110 it can be desirable to fix the location of the inner shaft 825 (and thus the bronchial isolation device in the housing 850) relative to the patient's body while proximally withdrawing the outer shaft 820 and the housing 850 relative to the bronchial passageway to eject the bronchial isolation device, as shown in FIGS. 11A and 11B. Given that the outer shaft 820 moves proximally relative to the bronchial passageway during the foregoing process, the outer shaft 820 can encounter resistance to proximal movement due to friction with devices or body passageways in which the delivery device is positioned. For example, the outer surface of the outer shaft 820 can encounter frictional resistance against an anesthesia adaptor through which the outer shaft is inserted. The anesthesia adapter is a fitting that permits the bronchoscope and delivery catheter to be inserted into the lung without leakage of ventilated oxygen, anesthesia gases, or other airway gases. The adapter typically has a valve through which the delivery catheter or bronchoscope is inserted. The valve seals against the outer surface of the outer shaft 820 to prevent air leaks. This seal can provide resistance against proximal movement of the outer shaft 820 during ejection of the bronchial isolation device from the housing 850. Such resistance to proximal movement of the outer shaft 820 is undesirable, as it can result in the bronchial isolation device 115 being deployed in a location distal of the target location in the bronchial passageway.

Figure 21:
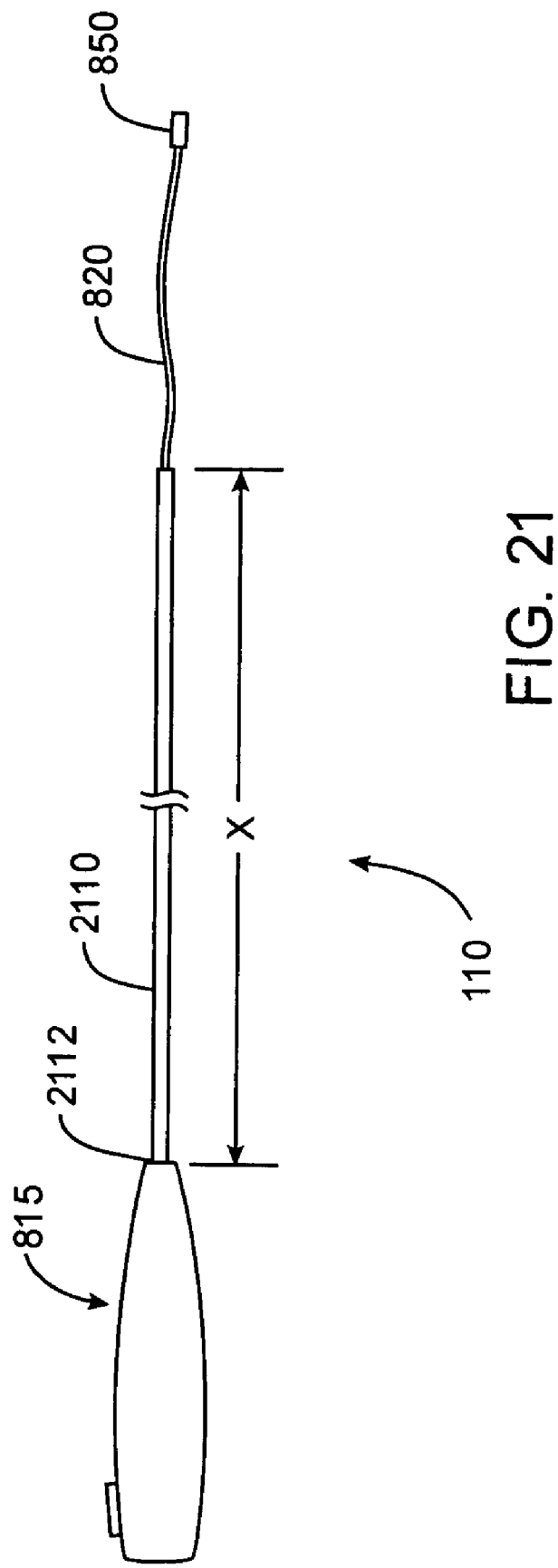
FIG. 21 shows an embodiment of the delivery catheter that includes a deployment sheath.

FIG. 21 shows an embodiment of the delivery catheter 110, which includes a deployment sheath 2110 that reduces or eliminates the resistance to proximal movement of the catheter outer shaft 820 during ejection of the bronchial isolation device 115. The deployment sheath 2110 is a sheath having an internal lumen in which the outer shaft 820 is slidably positioned. The sheath 2110 is fixed at a proximal end 2112 to the actuation handle 815. FIG. 21 shows the actuation handle 815, although the sheath 2110 can be used with any type of handle. Furthermore, it should be appreciated that the sheath 2110 is not limited to use with delivery catheters that deploy bronchial isolation devices, but can rather be used with various types of catheters. For example, the sheath configuration can be used in combination with catheters suitable for use in venous, arterial, urinary, biliary, or other body passageways. The sheath 2110 extends over the outer shaft 820 a distance X. The distance X can vary. In one embodiment, the distance X is long enough to extend to locations where the outer shaft is likely to encounter frictional resistance to movement, such as at the anesthesia adapter, if present. However, when used with a delivery catheter having a housing 850, the distance X is such that the distal end of the sheath does not interfere with the housing 850 being fully withdrawn in the proximal direction.

The sheath 2110 can have a very thin wall to minimize its contribution to the overall diameter of the delivery catheter 110. In one embodiment, the sheath 2110 has a wall thickness in the range of approximately 0.002 inches to approximately 0.004 inches. The sheath 2110 is manufactured of a material that is lubricous to minimize resistance to the outer shaft 820 sliding inside the sheath 2110. The sheath material also has a stiffness that resists crumpling when a compressive load is placed along the length of the sheath (such as when the sheath is possibly pinched or grabbed to fix its position relative to the anesthesia adapter during ejection of the catheter from the housing, as described below). The compressive forces can come from the possibility that the outer shaft is pinched when the sheath is pinched, and thus when the handle is actuated and the outer shaft starts to move towards the handle, the sheath is compressed]. The sheath 2110 can be manufactured of various materials, such as, for example, polyimide, Teflon doped polyimide, PolyEtherEtherKetone (PEEK), etc.

Figure 22:
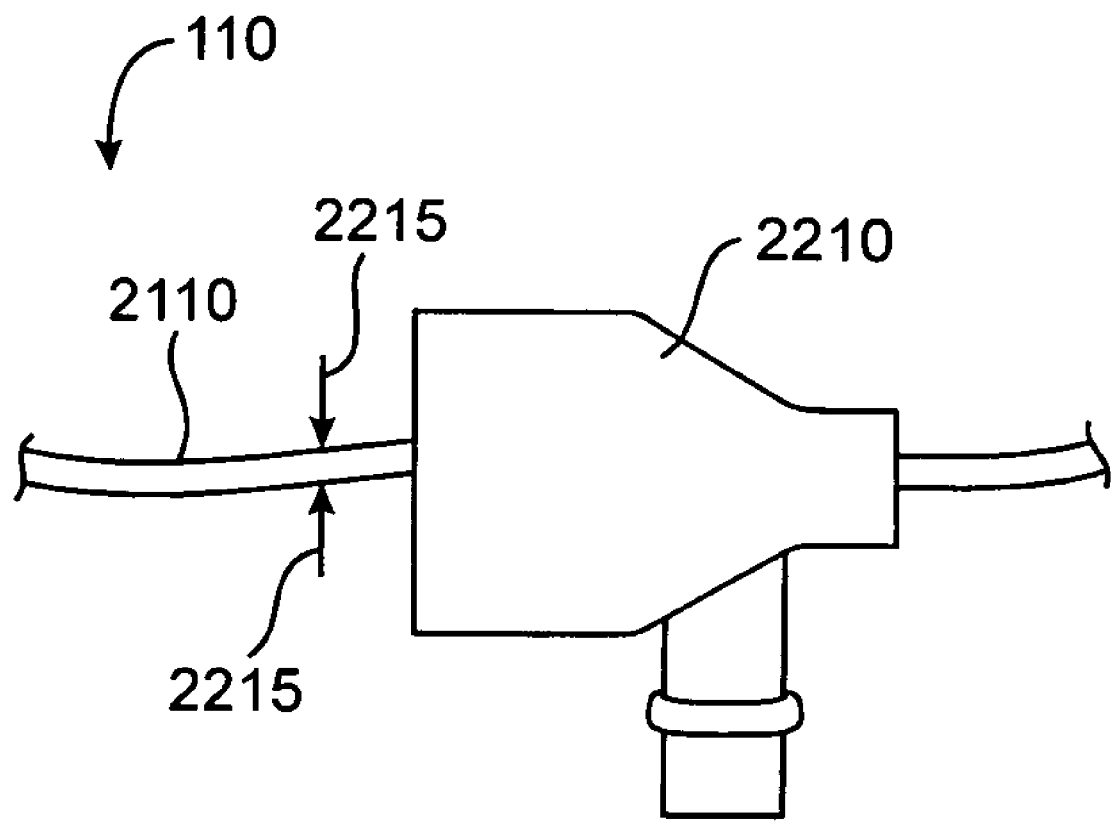
FIG. 22 shows a partial view of the delivery catheter of FIG. 21 positioned through an anesthesia adapter.

In use, the delivery catheter 110 is positioned in the patient's lung through the trachea, such as described above. This can involve the delivery catheter 110 being positioned through a device such as a bronchoscope or through an anesthesia adapter 2210, such as shown in the partial view of FIG. 22. The sheath 2110 is located between the anesthesia adapter 2210 and the outer shaft 820 (not shown in FIG. 22) such that the sheath 2110 provides a lubricous shield between the outer shaft 820 and the anesthesia adapter. Thus, the outer shaft 820 can be proximally moved using the actuation handle without the outer shaft 820 encountering frictional resistance from contact with the anesthesia adapter (or any other object or device in which the sheath and outer shaft are positioned). If desired, the operator can grab or pinch the catheter 110 (as represented by the arrows 2215 in FIG. 22) through the sheath 2110 at the entrance of the anesthesia adapter 2210 to fix the location of the sheath 2110 (and thus the location of the handle and the inner shaft) relative to the patient and/or anesthesia adaptor. As the sheath 2110 is made of a relatively rigid and lubricous material, the outer shaft 820 is free to slide through the sheath in the proximal direction as the sheath is grabbed.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed:

1. A device for sizing an inside diameter of a lung passageway and delivering a bronchial isolation device into the passageway, the device comprising:
   an elongate shaft configured for positioning in the lung passageway;
   a housing located at or near a distal end of the elongate shaft for housing the bronchial isolation device; and
   a sizing element disposed along the elongate shaft at or near the housing, the sizing element comprising a plurality of transverse extensions, wherein each extension has a fixed length, and wherein said plurality of extensions comprises:
      two long transverse extensions disposed approximately opposite one another across the shaft, wherein a first length from a tip of one long extension to a tip of the other long extension corresponds to a maximum diameter of the lung passageway in which the bronchial isolation device may be functionally delivered; and
      two short transverse extensions disposed approximately opposite one another across the shaft, wherein a second length from a tip of one short extension to a tip of the other short extension corresponds to a minimum diameter of the lung passageway in which the bronchial isolation device may be functionally delivered.

2. The device of claim 1, wherein at least part of the sizing element is disposed on the housing.

3. The device of claim 2, wherein the long extensions and the short extensions are disposed on the housing.

4. The device of claim 1, wherein the sizing element further comprises a depth measuring extension comprising an elongate post that extends axially from the distal end of the elongate shaft, wherein the elongate post has a length that is substantially equal to a length of a portion of the bronchial isolation device that contacts the bronchial lumen wall when the bronchial isolation device is implanted in the lung passageway.

5. The device of claim 4, further comprising a handle on a proximal end of the elongate shaft, the handle having a hole sized to receive the depth measuring to facilitate storage of the device.

6. The device of claim 1, wherein the transverse extensions are flexible such that the extensions can be folded back against the elongate shaft during insertion of the device through a lumen of a delivery device.

7. A device for sizing an inside diameter of a lung passageway and delivering a bronchial isolation device into the passageway, the device comprising:
   an elongate shaft configured to be entered into the lung passageway via a bronchoscope;
   a housing located at or near a distal end of the elongate shaft for housing the bronchial isolation device; and
   a sizing element disposed at or near the distal end of the shaft, the sizing element comprising a plurality of transverse extensions, wherein each extension has a fixed length and provides an indication as to the size of the lung passageway to allow a user to determine whether the passageway has a diameter suitable for delivery of the bronchial isolation device.

8. The device of claim 7, wherein the sizing element defines a range of transverse dimensions that correspond to a minimum diameter and a maximum diameter in which the bronchial isolation device can be functionally deployed, and wherein the extensions are disposed to be viewed via the bronchoscope to determine the suitability of the bronchial isolation device for use in the lung passageway.

9. The device of claim 7, wherein the sizing element comprises at least two long extensions, and two short extensions, the length of the long extensions corresponding to the maximum diameter of the lung passageway and, the length of the short extensions corresponding to a minimum diameter of the lung passageway.

10. The device of claim 7, wherein the sizing element comprises a first set of two extensions disposed on the shaft, wherein the first extensions define a length substantially equal to a largest possible diameter for a bronchial passageway in which the bronchial isolation device can be used.

11. The device of claim 10, wherein the sizing element further comprises a second set of two extensions disposed on the shaft, wherein the second extensions define a length substantially equal to a smallest possible diameter for a bronchial passageway in which the bronchial isolation device can be used.

12. The device of claim 11, wherein the sizing element further comprises a third set of two extensions disposed on the shaft, wherein the third extensions define a length substantially equal to a transition diameter between a pair of differently-sized bronchial isolation devices.

13. The device of claim 7, wherein the sizing element comprises a depth measuring extension comprising an elongate post that extends axially from the distal end of the shaft, wherein the elongate post has a length that is substantially equal to a length of a portion of the bronchial isolation device that contacts the bronchial lumen wall when the bronchial isolation device is implanted in the lung passageway.

14. The device of claim 13, further comprising a handle on a proximal end of the elongate shaft, the handle having a hole sized to receive the depth measuring to facilitate storage of the device.

15. The device of claim 7, wherein the extensions are flexible such that the extensions can be folded back against the elongate shaft during insertion of the device through a lumen of a delivery device.

* * * * *